United States Patent [19]
Gonzalez-Cadavid et al.

[11] Patent Number: 6,133,281
[45] Date of Patent: Oct. 17, 2000

[54] NMDA RECEPTOR BLOCKERS IN THE THERAPY OF UROGENITAL DISEASE

[75] Inventors: Nestor F. Gonzalez-Cadavid, Pasadena; Jacob A. Rajfer, Rolling Hills Estates, both of Calif.

[73] Assignee: Harbor-UCLA Research and Education Institute, Torrance, Calif.

[21] Appl. No.: 08/956,907

[22] Filed: Oct. 23, 1997

Related U.S. Application Data

[60] Provisional application No. 60/029,250, Oct. 24, 1996.

[51] Int. Cl.$^7$ .......................... A61K 31/13; A61K 31/135; A61K 31/4748
[52] U.S. Cl. ........................... 514/289; 514/579; 514/647
[58] Field of Search ..................................... 514/289, 579, 514/647

[56] References Cited

U.S. PATENT DOCUMENTS 5,162,311  11/1992  Herrling et al. ......................... 514/110

FOREIGN PATENT DOCUMENTS

93/07903  4/1993  WIPO .

OTHER PUBLICATIONS

Achari R, Laddu A (1993) Terazosin: A New Alpha Adrenoceptor Blocking Drug. *J. Clin Pharmacol* 32:520–523.
Albers GW, et al., (1995) Safety, Tolerability and Pharmacokinetics of the N–Methyl–D–Aspartate Antagonist Ro–01–6794/706 in Patients with Acute Ischemic Stroke. *Annals NY Academy of Sciences* :250–261.
Bessho Y, et al., (1993) Glutamate receptor agonists enhance the expression of BDNF mRNA in cultured cerebellar granule cells. *Brain Res Mol Brain Res* 18:201–208.
Bourguignon JP, et al., (1993) Control of pulsatile secretion of gonadotrophin releasing hormone from hypothalamic explants. *Human Reproduction* 2:18–22.
Brann DW, et al., (1993) Steroid Hormone Effects on NMDA Receptor Binding and NMDA Receptor mRNA Levels in the Hypothalamus and Cerebral Cortex of the Adult Rat. *Neuroendocrinology* 58:666–672.
Catalona WJ (1994) Management of Cancer of the Prostate. *New England Journal of Medicine* 331:996–1004.
Dehpour AR, et al., (1995) Different Calcium Dependencies of Contractile Activity of Prostatic and Epididymal Portions of Rat Vas Deferens. *Gen. Pharmac.* 26:633–639.
D'Ercole AJ, et al., (1994) Tissue concentrations of somatomedin C: Further evidence for mlutiple sites of synthesis and paracrine or autocrine mechanisms of action. *Proc Natl Acad Sci USA* 81:935–939.
Doble, A (1995) Excitatory amino acid receptors and neurodegeneration. *Therapie* 50:319–337.
Fallon, B (1995) Intracavernous Injection Therapy for Male Erectile Dysfunction. *Urologic Clinics of North America* 22:883–845.
Feldman HA, et al., (1994) Impotence and Its Medical and Psychosocial Correlates: Results of the Massachusetts Male Aging Study. *The Journal of Urology* 151:54–61.

Garban H, et al., (1995) Restoration of Normal Adult Penile Erectile Response in Aged Rats by Long–Term Treatment with Androgens. *Biology of Reproduction* 53:1365–1372.
Garbán H, et al., (1995) Effect of aging on nitric oxide–mediated penile erection in rats. *American Journal of Physiology* 268:H467–H475.
Garbán H, et al., (1997) Cloning of Rat and Human Inducible Penile Nitric Oxide Synthase. Application for Gene Therapy of Erectile Dysfunction. *Biology of Reproduction* 56:954–963.
Giorda C, et al., (1995) Alpha–1 Blocker Doxazosin Improves Peripheral Insulin Sensitivity in Diabetic Hypertensive Patients. *Metabolism* 44:673–676.
Grimwood S, et al., (1996) Generation and Characterisation of Stable Cell Lines Expressing Recombinant Human N–Methyl–D–Aspartate Receptor Subtypes. *Journal of Neurochemistry* 66:2239–2247.
Guh J–H, et al., (1995) Characterization of Alpha–1 adrenoceptor subtypes in tension response of human prostate to electrical field stimulation. *J Pharmacol* 115:142–146.
Hung A, et al., (1995) Expression of Inducible Nitric Oxide Synthase in Smooth Muscle Cells From Rat Penile Corpora Cavernosa. *J Androl* 16:469–481.
Ishii T, et al., (1993) Molecular Characterization of the Family of the N–Methl–D–Aspartate Receptor Subunits. *The Journal of Biological Chemistry* 268:2836–2843.
Janknegt RA, et al., (1993) Efficacy and Safety of the Alpha–1 Blocker Doxazosin in the Treatment of Benign Prostatic Hyperplasia. *Eur Urol* 24:319–326.
Kornhuber J, et al., (1994) Amantadine and memantine are NMDA receptor antagonists with neuroprotective properties. *J Neural Transm* 43:91–104.
Kyncl JJ (1993) Pharmacology of Terazosin: An Alpha–1 Selective Blocker. *J Clin Pharmacol* 33:866–899.
Lee T–S, Hou X (1995) Vasoactive Effects of Ketamine on Isolated Rabbit Pulmonary Arteries. *Chest* 107:1152–1155.
Lepor H, et al., (1996) The Efficacy of Terazosin, Finasteride, or both in Benign Prostatic Hyperplasia. *New England Journal of Medicine* 335:533–539.
Levsin (hyoscyamine sulfate USP) (1997). *Physician's Desk Reference*, pp. 2405–2406.
Linet OI, et al., (1996) Efficacy and safety of intracavernosal Alprostad; 1 in men with erectile dysfunction. *New England Journal of Medicine* 334:873–877.
Lugg JA, et al., (1995) Dihydrotestosterone is the Active Androgen in the Maintenance of Nitric Oxide–Mediated Penile Erection in the Rat. *Endocrinology* 136:1495–1501.

(List continued on next page.)

*Primary Examiner*—Phyllis G. Spivack
*Attorney, Agent, or Firm*—Fulwider Patton Lee & Utecht, LLP

[57] ABSTRACT

Methods are presented for the treatment of benign prostatic hyperplasia. The methods provide for administration to a person at least one compound identified generically as antagonists of N-methyl-D-aspartate receptors. These compounds are selected from the group consisting of memantidine, amantidine, dextromethorphan and ketamine.

3 Claims, 18 Drawing Sheets

OTHER PUBLICATIONS

Lugg JA, et al., (1996) Cavernosal nerve stimulation in the rat reverses castration–induced decrease in penile NOS activity. *Am J Physiol* 34:354–361.

Magee T, et al., (1996) Cloning of a Novel Neuronal Nitric Oxide Synthase Expressed in Penis and Lower Urinary Tract. *Biochemical and Biophysical Research Communications* 226:141–151.

Matsumoto G, et al., (1995) Role of glutamate and NMDA receptors in the descencing limb of the spinobulbospinal micturition reflex pathway of the rat. *Neuroscience Letters* 183:58–61.

McCann SM (1997) The Nitric Oxide Hypothesis of Brain Aging. *Experimental Gerontology* 32:431–440.

Munir H, et al., (1996) Pharmacological and Immunological Characterization of N–methyl–D–aspartate Receptors in HumN Nt2–N Neurons. *Journal of Pharmacology and Experimental Therapeutics* 276:819–828.

Murray F, et al., (1995) Evaluation and Treatment of Erectile Dysfunction. *American Journal of the Medicial Sciences* 309:99–109.

Osterling JE (1995) Benign Prostatic Hyperplasia. Medical and Minimally Invasive Treatment Options. *Drug Therapy* 332:99–109.

Osterling JE, et al., (1994) A new reality for urology: Drugs that alleviate BPH symptoms. *Contemporary Urology* 6:2–10.

Penson DF, et al., (1996) Androgen and Pituitary Control of Penile Nitric Oxide Synthase and Erectile Function in the Rat. *Biology of Reproduction* 55: 567–574.

Persson K, et al., (1992) Effects of inhibition in the L–arginine/nitric oxide pathway in the rat lower urinary tract in vivo and in vitro. Br I Pharmacol 107:178–184.

Pedersen CM, et al., (1993) Smooth muscle relaxant effects of propofol and ketamine in isolated guinea–pig trachea. *European Journal of Pharmacology* 238:75–80.

Penson DF, et al., (1997) Adrenal Control of Erectile Function and Nitric Oxide Synthase in the Rat Penis. *Endocrinology*, 138(9), 1–8.

Rajfer J, et al., (1992) Nitric Oxide as a Mediator or Relaxation of the Corpus Cavernosum in Response to Nonadrenergic, Noncholinergic Neurotransmission. *New England Journal of Medicine* 326:90–94.

Said SI, (1995) N–Methyl–D–Aspartate Receptors Outside The Central Nervous System: Activation Causes Acute Lung Injury That is Mediated by Nitric Oxide Synthesis and Prevented by Vasoactive Intestinal Peptide. *Neuroscience* 65:943–946.

Saito M, et al., (1994) Effect of Partial Outflow Obstruction on Rat Detrusor Contractility and Intracellular Free Calcium Concentration. *Neurourology and Urodynamics* 13:297–305.

Saito M, et al., (1993) Effects of Partial Outlet Obstruction of the Rat Urinary Bladder on Micturition Characteristics, DNA Synthesis and the Contractile Response to Field Stimulation and Pharmacological Agents. *The Journal of Urology* 150:1045–1051.

Saito M, et al., (1993) Effect of Partial Outlet Obstruction on Contractility: Comparison Between Severe and Mild Obstruction. *Neurourology and Urodynamics* 12:573–583.

Steers WD (1993) Physiology of the Urinary Bladder. In *Campbells Urology*, pp. 142–176.

Sugihara H, et al., (1992) Structures and Properties of Seven Isoforms of the NMDA Receptor Generated by Alternative Splicing. *Biochemical and Biophysical Research Communications* 185:862–832.

Szabo L, et al., (1993) Voiding Disorders and Unstable Bladder in Children. *International Urology and Nephrology* 25:431–437.

Takeda M, et al., (1994) Effects of Nitric Oxide on Human and Canine Prostates. *Adult Urology* 45:440–446.

Testa S, et al., (1996) Functional Antagonistic Activity of REC 15/2739, a Novel Alpha–1 Antagonist Selective for Thomas RJ (1995) Excitatory Amino Acids in Health and Disease. *J Am Geriatr Soc* 43:1279–1289.

Thornberg SA, et al., (1996) A Review of NMDA Receptors and the Phencyclidine Model of Schizophrenia. *Pharmacotherapy* 16:82–93.

Tortella FC, et al., (1995) Dextromethorphan analogs are neuroprotective in vitro and block glutamate–induced excitotoxic calcium signals in neurons. *Neuroscience Letters* 198:79–82.

Trube G, et al., (1994) Dextromethorphan: Cellular Effects Reducing Neuronal Hyperactivity. *Epilepsia* 35:S62–S67.

Urwyler S, et al., (1996) Biphenyl–derivatives of 2–Amino–7–phosphono–heptonoic Acid, a Novel Class of Potent Competitive N–Methyl–D–aspartate Receptor Antagonists. I. Pharmacological Characterization in Vitro. *Neuropharmacology* 35:643–654.

Vernet D, et al., (1995) Reduction of Penile Nitric Oxide Synthase in Diabetic BB/WOR$^{dp}$ (Type I) and BBZ/WOR$^{dp}$ (Type II) Rats with Erectile Dysfunction. *Endocrinology* 136:5709–5717.

Walsh PC (1996) Treatment of Benign Prostatic Hyperplasia. *New England Journal of Medicine* 335:586–587.

Wein AJ (1993) Pharmacologic Management of Non–B-PH–Induced Voiding Dysfunction. *Monographs in Urology* 14:68–86.

Wendling WW, et al., (1996) The Effects of N–Methyl–D–Aspartate Agonists and Antagonists on Isolated Vocine Cerebral Arteries. *J Neurosurgical Anesthesia* 82:264–268.

Xie Y, et al., (1997) Effect of Long–Term Passive Smoking on Erectile Function and Penile Nitric Oxide Synthase in the Rat. *The Journal of Urology* 157:1121–1126.

Yoshiyama M, et al., (1995) Interactions between NMDA and AMPA/kainate receptors in the control of micturition in the rat. *European Journal of Pharmacology* 287:73–78.

Wenzel A, et al., (1995) Distribution of NMDA receptor subunit proteins NR2A, 2B, 2C and 2D in rat brain. *Neurochemistry* 7:45–48.

Hirota et al., Acta Anaesthesiologica Scandinavica, 39(2), 175–8 (abstract), Feb. 1995.

Hytrin, Physicians' Desk Reference, @ pp. 430–433 (1995).

Prinzide, Physicians' Desk Reference, @pp. 1740–1744 (1995).

NMDA RECEPTOR BLOCKERS IN THE THERAPY OF UROGENITAL DISEASE

RELATED APPLICATIONS

This is a continuation in part of provisional application Ser. No. 60/029,250 filed Oct. 24, 1996, entitled "RECEPTOR BLOCKERS IN THE THERAPY OF ABNORMAL PROSTATE GROWTH."

BACKGROUND OF THE INVENTION

1. Field of the Invention

This invention relates generally to methods for therapy of urogenital disease, and more particularly concerns methods for blocking N-methyl-D-aspartate receptors in urogenital organs, utilizing the response of these tissues to blockers of these receptors, and novel therapeutic uses for these drugs.

2. Description of Related Art

Prostate cancer is one of the most prevalent pathologies in men over 50 years of age and the most common internal cancer of males in the USA. Approximately 140,000 cases are newly diagnosed and about 30,000 die from the disease annually. Radical prostatectomy is the only treatment available to remove the malignant organ, while surgical or chemical androgen ablation is used to avoid or delay the onset of extraprostatic disease. The failure of surgical or medical treatment of prostate cancer is mostly due to the establishment of extraprostatic progression or metastasis, and the parallel progression of the tumor from androgen dependency to androgen unresponsiveness. As a result, androgen ablation fails to stop tumor growth and its spread. Treatment with chemotherapy or other types of drugs is not effective.

Benign prostatic hyperplasia (BPH), an abnormal non-malignant growth of the prostate leading to voiding obstruction and potential bladder instability, also afflicts 50% of men over the age of 50, and is one of the primary causes of hospitalization and surgical procedures in men. Transurethral resection ablation of the prostate (TURP) is one of the most common surgical procedures performed in the USA. The main clinical symptoms are obstructive in nature (decrease force of strain, hesitancy, incomplete voiding) as well as irritative (frequency, urgency, dysuria, nocturia). This is due to partial occlusion of the prostatic urethra by the enlarged prostate, combined with an increase in the tone (contraction) of the prostatic smooth muscle, and in certain cases hypertrophy of the bladder muscle (detrusor). Medical treatment of BPH is based on mainly drugs affecting either prostate growth or tone, with efficacy limited to a fraction of patients and undesirable side effects.

Bladder instability due to involuntary contractile episodes of the detrusor muscle, leading to urge incontinence without stress incontinence, is very common in the elderly population, particularly women. Bladder hyperreflexia due to neurological lesions is also common in this patient population. Both types of disorders may be treated medically with relaxants of the detrusor that facilitate urine storage. However, the drugs are effective in less than one third of patients and often at the cost of substantial side effects.

Erectile dysfunction, which is the impairment of penile smooth muscle relaxation impeding the rigidity necessary for penetration during sexual intercourse, is responsible for most clinically diagnosed cases of impotence (12–15 million men in the US). Organic impotence is associated with vascular disease, diabetes, hypertension, and aging. In the adult onset, insulin-independent type II diabetes mellitus, about 2 million men are assumed to suffer from organic impotence. Erectile dysfunction leads to impotence in up to 75% of adult patients with over 5 years of types I or II diabetes. The incidence of impotence risk factors increases with aging, and in healthy elderly men it may be due to loss of compliance of the penile smooth muscle unrelated to clinically defined vasculopathy or neuropathy. Current medical treatment is based on the delivery into the corpora cavernosa of vasoactive substances that relax the corporal smooth muscle, such as cGMP phosphodiesterase inhibitors, adenylate cyclase stimulators, or alpha-adrenergic blockers. This therapy is not curative and may have side effects for some patients, mainly mild pain, priapism, and corporal fibrosis.

The excitatory amino acids (EAA), L-glutamate, L aspartate, and other related metabolites, exert their neurotransmission effects by acting on receptors located on virtually all neurons in the central nervous system. These receptors, designated with the generic name of glutamate receptors belong to two categories: a) ionotropic, that are directly coupled to membrane sodium or calcium channels; and b) metabotropic, that are coupled with G proteins triggering the arachidonic acid cascade and changes in cAMP.

The N-methyl-D-aspartate receptors (NMDAR) are designated as such because they bind the synthetic aspartate analog N-methyl-D-aspartate (NMDA) and belong to the ionotropic receptors class together with the non-NMDAR (kainate and AMPA receptors). The NMDAR have been identified directly so far only in postsynaptic neurons in the brain and lung tissues, although because of the effects of some NMDAR blockers on the relaxation of arteries and smooth muscle it may be inferred they may be present in other locations. By glutamate orNMDA binding these receptors trigger a Ca2+ influx into the cells that activates a series of Ca2+ dependent cascades, among them nitric oxide synthase (NOS), the enzyme that synthesizes nitric oxide (NO), a pleiotropic neurotransmitter and physiological mediator. NO produced by EAA binding to NMDAR may have dual effects according to its concentration and tissue location. At small doses NO may either diffuse to presynaptic neurons and act as a retrograde messenger, or presumably to blood vessel smooth muscle causing vasodilation. In contrast, at very high doses the NMDAR- triggered NO can induce cytotoxicity, as is further explained below.

The EAA/NMDAR interaction also affects the hypothalamic control of LH pulses and GnRH release in rats in a sex-dependent and presumably NO-mediated manner. This indicates that some of the actions of NMDAR blockers can involve the hypothalamic axis. In addition, EAA/NMDAR can stimulate the release of growth factors and elicit the expression of c-fos protein, a critical step in the early stages of cell proliferation. There are no publications on whether NMDARs play a role in cancer growth or progression in general. MK-801 (noncompetitive, high affinity) and other NMDA blockers have been extensively studied as neuro-protective agents in the treatment of stroke, epilepsy, pain, Parkinson's disease, etc. Many of them are in clinical use and their safety is well evaluated.

Demonstration of NMDARs in the urogenital system has not been previously reported, with isolated exceptions (e.g., indirect evidence on lung and skeletal muscle), outside the central nervous system. The prevalent view is that prostatic tone is controlled mainly by alpha adrenergic receptors, whereas cholinergic and adrenergic pathways regulate bladder tone. The nitric oxide-dependent NANC neurotransmission is not known to be very significant in the prostate, and it is controversial in the case of the bladder, as assessed by organ bath studies. Therefore, the most efficient drugs available in the clinic for prostate and bladder relaxation have been the alpha-adrenergic blockers and anticholinergic agents, respectively.

Recent reports indicated that the NMDAR blocker MK-801 has been tested in rats (intravenously or intrathecally), resulting in an inhibition of bladder contractions in a dose dependent manner, and the investigators have assumed that both AMPA/kainate and NMDA glutamate receptors are important in the micturition reflex pathway. However, these effects have been ascribed exclusively to the spinal cord, and no inference has been made to the presence of these receptors in either the bladder or the prostate.

It would be desirable to provide therapy for urogenital disease utilizing NMDARs that are present in the bladder and prostate to contribute to the tone of these organs, and to utilize NMDAR antagonists to relax the smooth muscle of both bladder and prostate, and presumably the urethra.

Penile tone can also be controlled physiologically by the balance of relaxing and contractile agents. Among the former group, NO is considered to be the mediator of the erectile response through the stimulation of the intracavernosal synthesis of CGMP that leads to the decrease in intracellular Ca2+ and smooth muscle relaxation. However, ancillary pathways causing a similar mobilization of intracellular Ca2+ can operate in the corpora cavernosa. It would therefore be desirable to provide therapies utilizing NMDARs that are present and active in the penis, to elicit a Ca2+ influx, and NMDAR blockers to cause corporal smooth muscle relaxation.

Studies on the central nervous system suggest the opposite view, however, that excitatory amino acids in vivo would cause corporal relaxation through their effects on spinal NMDA receptors, based on experiments showing that MK-801 decreases the erectile response in the anesthetized rat. However, this is opposite to the well established effects of NMDA receptors on Ca2+ channels, and if confirmed would suggest an indirect mechanism on the smooth muscle triggered by spinal NMDA receptors centrally acting on other pathways. The observed effects on the erectile response have been ascribed generally exclusively to the spinal cord.

It would be desirable to provide novel methods of treatment and compounds for the treatment of prostate cancer, benign prostatic hyperplasia, bladder dysfunction in both men and women, erectile dysfunction, and other urogenital disease. Compounds are needed that affect at least the prostate, bladder, and/or the penile corpora cavernosa, and at least in the case of one of them, act simultaneously on the muscle tone and tissue growth (prostate), and there is a need for agents that are safe, with tolerable side-effects. The present invention meets these needs.

SUMMARY OF THE INVENTION

Briefly, and in general terms, the present invention provides for novel methods of treatment, and compounds for the treatment of prostate cancer, benign prostatic hyperplasia, bladder dysfunction in both men and women, erectile dysfunction, and other urogenital disease. The proposed compounds affect at least the prostate bladder, and, or the penile corpora cavernosa, and at least in the case of one of them, act simultaneously on the muscle tone and tissue growth (prostate). These agents are safe, with tolerable side-effects, and are currently in use or in clinical trials for conditions different from those mentioned above. Their biochemical mechanism of action is well understood, although the mechanism by which they trigger their effects locally by interacting with receptors in the urogenital system is not known. These compounds are useful for the treatment of prostate cancer, benign prostatic hyperplasia, bladder dysfunction in both men and women, and erectile dysfunction, among others.

The invention accordingly provides for a method for treating the abnormal growth of prostatic tissue in men with benign prostatic hyperplasia (BPH), or the urinary voiding dysfunction derived from this disease, based on single or multiple injections, continuous infusion, intraurethral delivery, prostate/urethral lavage or irrigation, or topical or oral administration, of compounds identified generically as antagonists of the NMDAR, given as single agents or in combination. These agents include drugs active against the following NMDAR sites: transmitter (such as D-AP-7, pentamidine, and all others active on this site); polyamine (ifenprodil, and all others active on this site); ion channel, low affinity (memantidine, amantidine, dextromethorphan, ketamine, and all others active on this site); ion channel, high affinity (dizocilpine or MK-801, and all others active on this site), or drugs active against additional sites of the NMDAR, which induce the relaxation or inhibits the abnormal growth of prostatic tissue, by acting either locally on NMDARs in this tissue or systemically through any other mechanism.

In another aspect, the invention provides for a method for treating the neoplastic growth of prostatic tissue in men with prostate cancer at any stage of the disease, based on single or multiple injections, continuous infusion, intraurethral delivery, prostate/urethral lavage or irrigation, or topical or oral administration, of compounds identified generically as antagonists of the NMDAR, given as single agents or in combination. These agents include drugs active against the following NMDAR sites: transmitter (such as D-AP-7, pentamidine, and all others active on this site); polyamine (ifenprodil, and all others active on this site); ion channel, low affinity (memantidine, amantidine, dextromethorphan, ketamine, and all others active on this site); ion channel, high affinity (dizocilpine or MK-801, and all others active on this site), or drugs active against additional sites of the NMDAR, which induce the relaxation or inhibits the neoplastic growth of prostatic tissue, by acting either locally on NMDARs in this tissue or systemically through any other mechanism.

In another embodiment, the invention provides for a method for treating urinary voiding dysfunction conditions in men or women, including incontinence, bladder instability, outlet obstruction, and related, based on single or multiple injections, continuous infusion, intraurethral delivery, bladder, prostate or urethral lavage or irrigation, or topical or oral administration, of compounds identified generically as antagonists of the NMDAR, given as single agents or in combination. These agents include drugs active against the following NMDAR sites: transmitter (such as D-AP-7, pentamidine, and all others active on this site); polyamine (ifenprodil, and all others active on this site); ion channel, low affinity (memantidine, amantidine, dextromethorphan, ketamine, and all others active on this site); ion channel, high affinity (dizocilpine or MK-801, and all others active on this site), or drugs active against additional sites of the NMDAR. which induce the relaxation of the bladder or the urethra by acting locally on NMDARs in this tissue.

The invention further provides for a method for treating erectile dysfunction or sexual impotence in men, based on single or multiple injections, continuous infusion, intraurethral delivery, bladder, prostate or urethral lavage or irrigation, or topical (lotions, creams, ointments, patches, or similar) or oral administration, of compounds identified generically as antagonists of the NMDAR, given as single agents or in combination. These agents include drugs active against the following NMDAR sites: transmitter (such as D-AP-7, pentamidine, and all others active on this site); polyamine (ifenprodil, and all others active on this site); ion channel, low affinity (memantidine, amantidine, dextromethorphan, ketamine, and all others active on this site); ion channel, high affinity (dizocilpine or MK-801, and all others active on this site), or drugs active against additional sites of the NMDAR, which induce the relaxation of the penile corpora cavernosa by acting locally on NMDARs in this tissue.

In a presently preferred embodiment, the invention utilizes derivatives of NMDAR blockers unable to pass the blood brain barrier, which exhibit binding capacity to NMDARs in prostate and bladder tissue, without undesirable effects on the central nervous system.

In another presently preferred embodiment, the invention utilizes agents which would target on specific subtypes of the NMDARs in the urogenital system, or would modulate their expression and or activity by chemical or biological means differentially from NMDAR subtypes present in the central nervous system.

These and other aspects and advantages of the invention will become apparent from the following detailed description and the accompanying drawings, which illustrate by way of example the features of the invention.

DETAILED DESCRIPTION OF THE PREFERRED EMBODIMENTS

Figure 1:
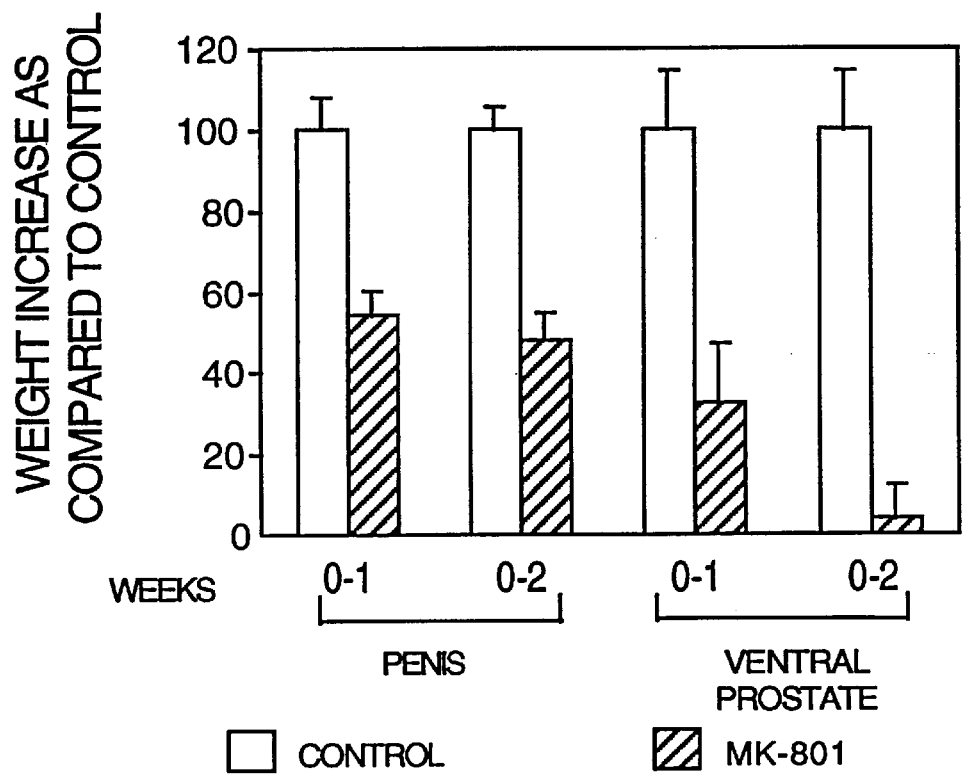
FIG. 1 shows the effect of NMDAR blockade by MK-801 in immature rats on penile and prostate growth.

The failure of surgical or medical treatment of prostate cancer is mostly due to the establishment of extraprostatic progression or metastasis, and the parallel progression of the tumor from androgen dependency to androgen unresponsiveness. Androgen ablation fails to stop tumor growth and its spread, and treatment with chemotherapy or other types of drugs is frequently not effective. Medical treatment of BPH by drugs affecting either prostate growth or tone has limited efficacy, and produces undesirable side effects. Drugs used for treatment of bladder instability are also typically effective in less than one third of patients and often at the cost of substantial side effects. Current medical treatment of erectile dysfunction is also frequently not curative and may cause side effects for some patients, such as pain, priapism, and fibrosis. The most efficient drugs available in the clinic for prostate and bladder relaxation have been the alpha-adrenergic blockers and anticholinergic agents, respectively.

Accordingly, as is illustrated in the drawings, the invention is embodied in novel methods and compounds for the treatment of prostate cancer, benign prostatic hyperplasia, bladder dysfunction in both men and women, erectile dysfunction, and other urogenital disease.

It has been found that dizocilpine, or MK-801, a member of a family of existing drugs acting as NMDAR blockers, is able to inhibit in vivo the normal growth of the ventral prostate in both sexually immature and adult rats, without affecting significantly body weight or the size of non-prostatic organs. This process in the adult rats occurs via a mechanism that does not appear to involve the blockade of the hypothalamic-pituitary-gonadal axis, since serum T, LH, or IGF1 were not significantly reduced by NMDAR inhibition.

The effects of NMDAR blockers on the prostate are most likely mediated by NMDAR and not by a receptor-unrelated mechanism. NMDARs have not yet been reported in the urogenital system, but they are detected in the present work as proteins immunoreacting on western blots with antibodies against one of the subunits of the rat brain NMDAR, in both the rat and human prostate. The NMDAR protein was also detected in the rat and human bladder and penis extracts, and the receptor itself was detected by NMDAR binding. The rat NMDAR in the urogenital tract is smaller than in the central nervous system (brain cortex, hypothalamus).

Several NMDAR blockers are able to relax in vitro in organ bath isolated tissue strips from the rat and human bladder body (detrusor) pre-contracted with bethanechol. The bladder preparations showed good contractile response to electrical field stimulation (EFS), and the relaxation could not be counteracted by bethanechol, EFS, methylene blue, atropine/guanethidine, or L-NAME, but it was completely reversible after washing. The bladder tissue can experience a series of successive contraction (bethanechol)/relaxation (NMDA blockers) cycles. Excitatory amino acids, such as NMDA and, to a lower extent glutamate, induce short and low intensity contractile responses.

The NMDAR blockers are also able to relax in vitro in organ bath isolated tissue strips from the human prostate (transitional zone) pre-contracted with norepinephrine. They induce the same reversible effects seen in the bladder and counteract EFS or norepinephrine additional increase in concentration. The mechanism is a NO-independent NANC pathway. The potency of some of these agents was in the range of that of terazosin, one of the drugs currently used for the treatment of BPH.

Many synaptic antagonists of the NMDAR acting on different sites of this receptor are active as bladder and prostatic relaxants. They include: 2-amino-5-phosphovalerate and pentamidine at the NMDAR transmitter site, ifenprodil at the glycine and polyamine sites, MK-801 as a high affinity uncompetitive antagonist of the ion channel, and dextromethorphan, amantidine, memantidine, and ketamine as low affinity uncompetitive antagonists of the ion channel. NMDAR antagonists are able to relax in vitro in organ bath isolated tissue strips from the human corpora cavernosa pre-contracted with phenylephrine. The corpora cavemosa preparations showed good NO-mediated relaxation response to electrical field stimulation (EFS) in the presence of guanethidine and atropine, as expected from NANC neurotransmission. However, the relaxation induced by the NMDA blockers was not counteracted by guanethidine/atropine indicating a non adrenergic-non cholinergic (NANC) response, and by L-NAME in the presence of these inhibitors, indicating a non-NO-mediated mechanism. The in vitro relaxing potency of some of these agents was in the range of that of prostaglandin E1 (PGE 1), one of the drugs currently used for the treatment of erectile dysfunction.

Many synaptic antagonists of the NMDA receptor acting on different sites of this receptor are active as corporal relaxants. They include, ifenprodil, MK-801, dextromethorphan, and ketamine, as defined above. However, 2-amino-5-phosphovalerate, acting at the NMDA transmitter site, was not effective On the basis of these findings, it can be concluded that NMDARs are present in the bladder, prostate, corpora cavernosa, and presumably in other urogenital organs, in the nerve terminals, and/or in other cell types; and therefore NMDARs are not confined to the central nervous system, spinal cord, or occasional organs where they were previously detected (lung). NMDARs in at least the prostate, bladder, and penis, would be responsible for a novel non adrenergic-non cholinergic (NANC), nitric oxide-independent, contraction/relaxation pathway, where excitatory amino acids or other ligands of the NMDAR act as local physiological regulators independently from their effects on the hypothalamus, other central nervous system regions, and spinal cord.

MK-801 and the other compounds studied, and by extension most, if not all, the NMDAR blockers should inhibit prostate cancer growth and metastasis irrespective of androgen dependence. Therefore, these drugs, many of them in clinical use or trials for non cancer-related conditions, are applicable for the therapy of advanced prostate cancer, by themselves or in combination with other drugs.

Similarly, these compounds should be effective in inhibiting abnormal prostate growth in BPH without the undesirable side-effects caused by 5a-reductase blockers, while simultaneously inhibiting the prostatic tone and alleviating the obstructive or irritative symptoms with an efficacy at least comparable to the current alpha-1-adreno receptor blockers.

Agents in this study should correct bladder instability and incontinence in non-BPH voiding conditions, mainly in the elderly population, and also in patients afflicted by spinal cord injury and other disorders, probably better than the clinically used anticholinergic drugs.

The possible existence of a common relaxation pathway for both the prostate and the bladder as stated above implies that agents affecting this mechanism should be active on both organs. At this moment, the clinical significance of this possibility cannot be assessed. However, it is proposed that dosage studies may reveal a differential response, and in addition, that ancillary pharmacological treatment to facilitate bladder emptying may compensate for the effect on the detrusor muscle.

Most of the NMDAR blockers should be effective in ameliorating erectile dysfunction associated with different conditions, such as diabetes, hypertension, aging, etc., at least comparably to the agents currently used.

NMDAR blockers should be given locally to the target organs, by injection, intraurethrally, topically, lavage, or other means that would minimize systemic distribution. This is because of the ability of NMDAR blockers to act directly on the target organs, and the possibility that the inhibition of centrally mediated effects elicited through hypothalamic or spinal receptors could oppose the desired cavernosal relaxation.

Derivatives of NMDAR blockers unable to pass the blood brain barrier should be selected for clinical trials, because they should retain the binding capacity to NMDARs in prostate and bladder tissue, without exhibiting undesirable effects on the central nervous system.

The urogenital organs may have specific subtypes of the NMDARs that may be amenable to tissue-specific biological manipulation, or used as targets for blockers less active on the NMDAR subtypes present in the central nervous system.

The advantages of NMDA blockers, among others, are storage stability, low cost, bypass of potentially affected pathways, reduction of side effects, activity on relaxation pathways different from the ones which arc target for existing drugs.

EXAMPLE 1

This example demonstrates that the blockade of the NMDAR by an antagonist, such as MK-801, can arrest the growth of the normal prostate in the rat by a mechanism that does not involve the hypothalamic/gonadal/pituitary axis.

Sexually immature (3.5 weeks old) Sprague Dawley male rats were treated twice daily with a subcutaneous injection of MK-801 at a dose of 0.15 mg/kg body weight dissolved in saline (treated), or of saline only (control), and animals were sacrificed under anesthesia at 1 and 2 weeks (N=8 per group). Another group was sacrificed at time 0 without any treatment and served as reference to obtain the initial weights for the growth curves. Blood was drawn from the heart and serum collected. Body weights were recorded and the prostate, testis, liver and bladder were excised, weighed, and stored at −70 C. Organ growth was determined by subtracting the time 0 weights from the similar values at 1 or 2 weeks. Testosterone (T), insulin-growth factor 1 (IGF-1), and luteinizing hormone (LH), were estimated in serum by conventional procedures.

FIG. 1, right section, shows that the NMDAR antagonist reduces considerably prostate growth at one week, and blocks it completely at 2 weeks (N=8), when compared with rats injected with saline only. Growth of another androgen-sensitive organ, the penis, was affected to a much lower extent (FIG. 1, left section), and the growth values for testis, liver, and body were reduced only slightly (not shown).

Figure 2:
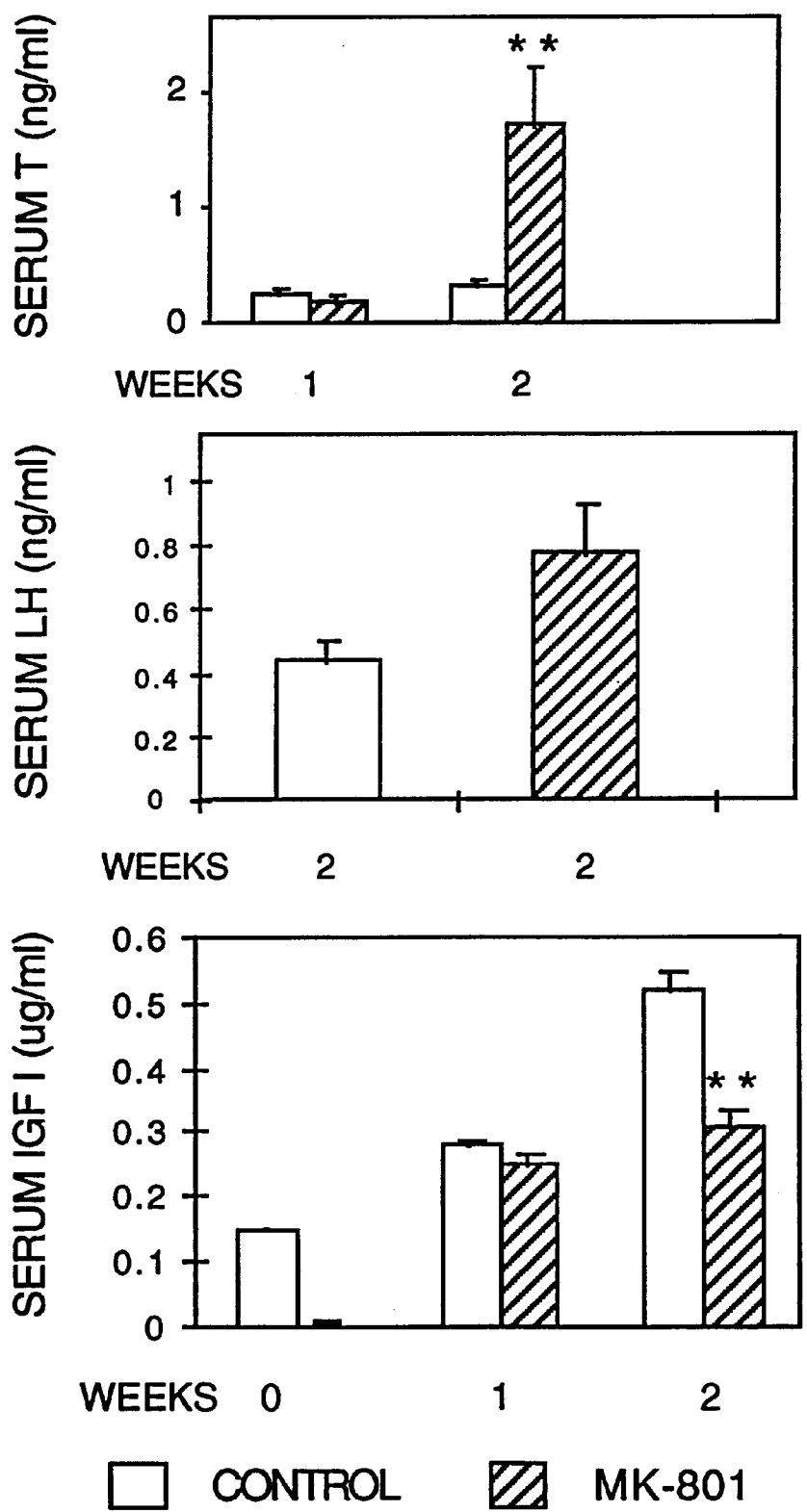
FIG. 2 shows the effect of NMDAR blockade by MK-801 in immature rats on serum T, LH, and IGF-1.

FIG. 2 shows that the effects of MK-801 on the growth of prostate and penis are not exerted by hypothalamic/gonadal blockade, because neither T (top), nor LH (medium), were reduced either at 1 or 2 weeks of treatment. However, serum IGF-1 (bottom) was significantly reduced after 2 weeks.

In another experiment, this experimental paradigm was repeated in adult (4 month-old) Sprague Dawley male rats (N=8 per group), but administering MK-801 over 2 weeks by continuous infusion with subcutaneously implanted min-iosmotic Alza pumps (0.5/hr μl/day of a solution containing 10 μg/μl; equivalent to 1.5 mg/kg/day), and sacrificing only at 2 weeks. The determinations were performed as above, against the time zero group.

Figure 3:
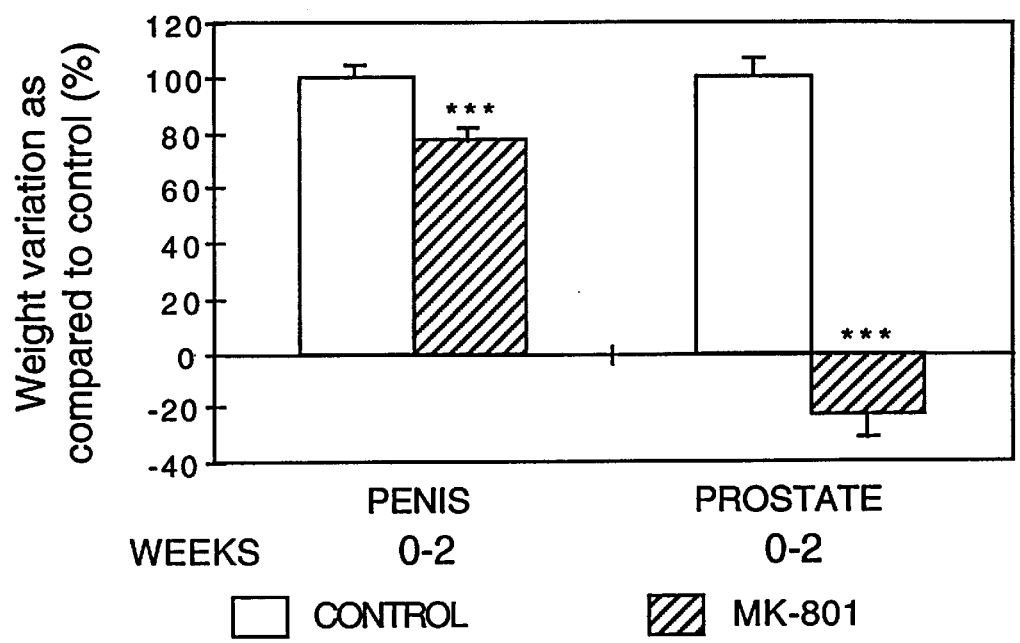
FIG. 3 shows the effect of NMDAR blockade by MK-801 in adult rats on penile and prostate growth.

FIG. 3 shows that the inhibition of prostatic growth was total, and even there seems to be a moderate involution (right section). In contrast, growth of the androgen-dependent organ used as reference, the penis (left section), was only slightly reduced and the same occurred with the testis, liver, and body weights (not shown).

Figure 4:
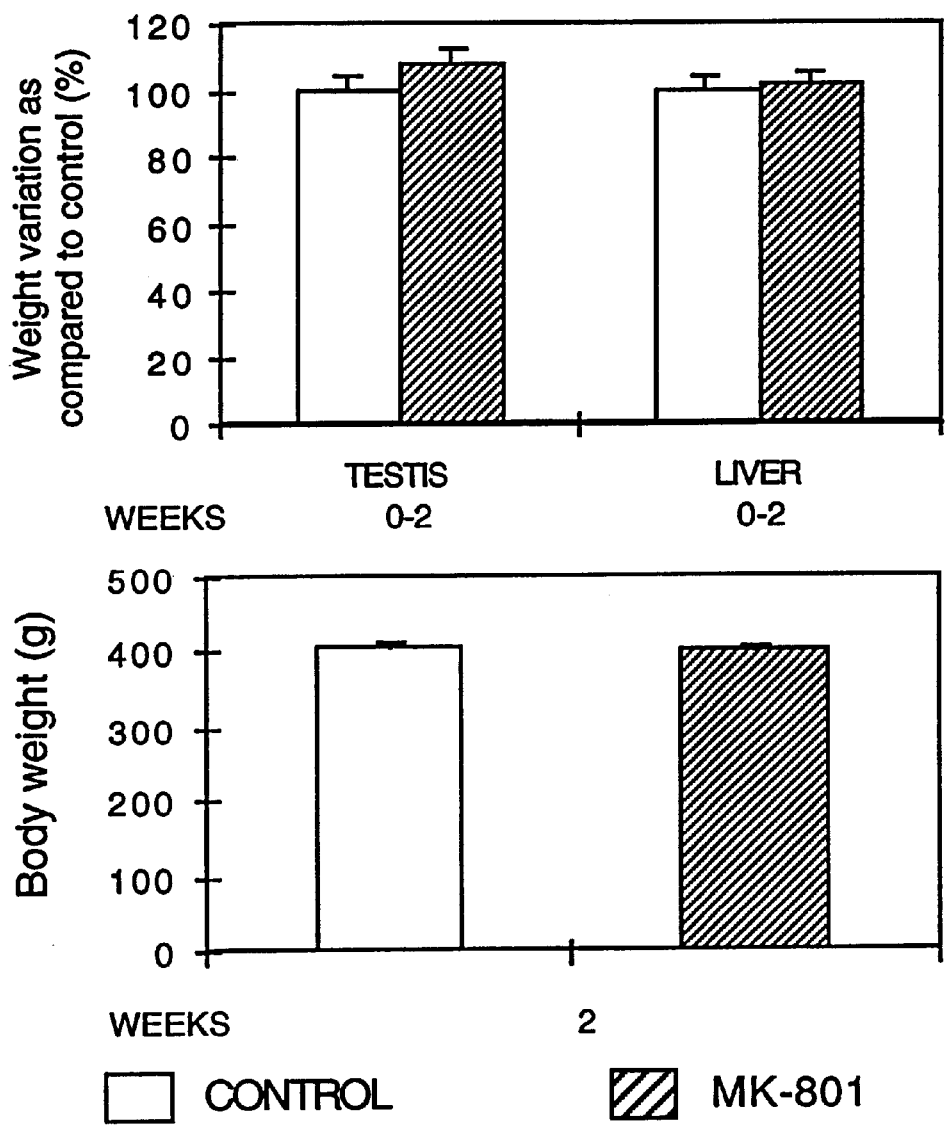
FIG. 4 shows the effect of NMDAR blockade by MK-801 in adult rats on testis, liver, and body growth.

FIG. 4 shows on the top panel that the increase of testis or liver weight occurring during 2 weeks in adult rats is not affected by treatment with MK-801, so that the reduction effect observed in the case of the prostate is specific for this organ. The bottom panel shows that at the completion of the 2 week experiment there is no variation in body weight.

Figure 5:
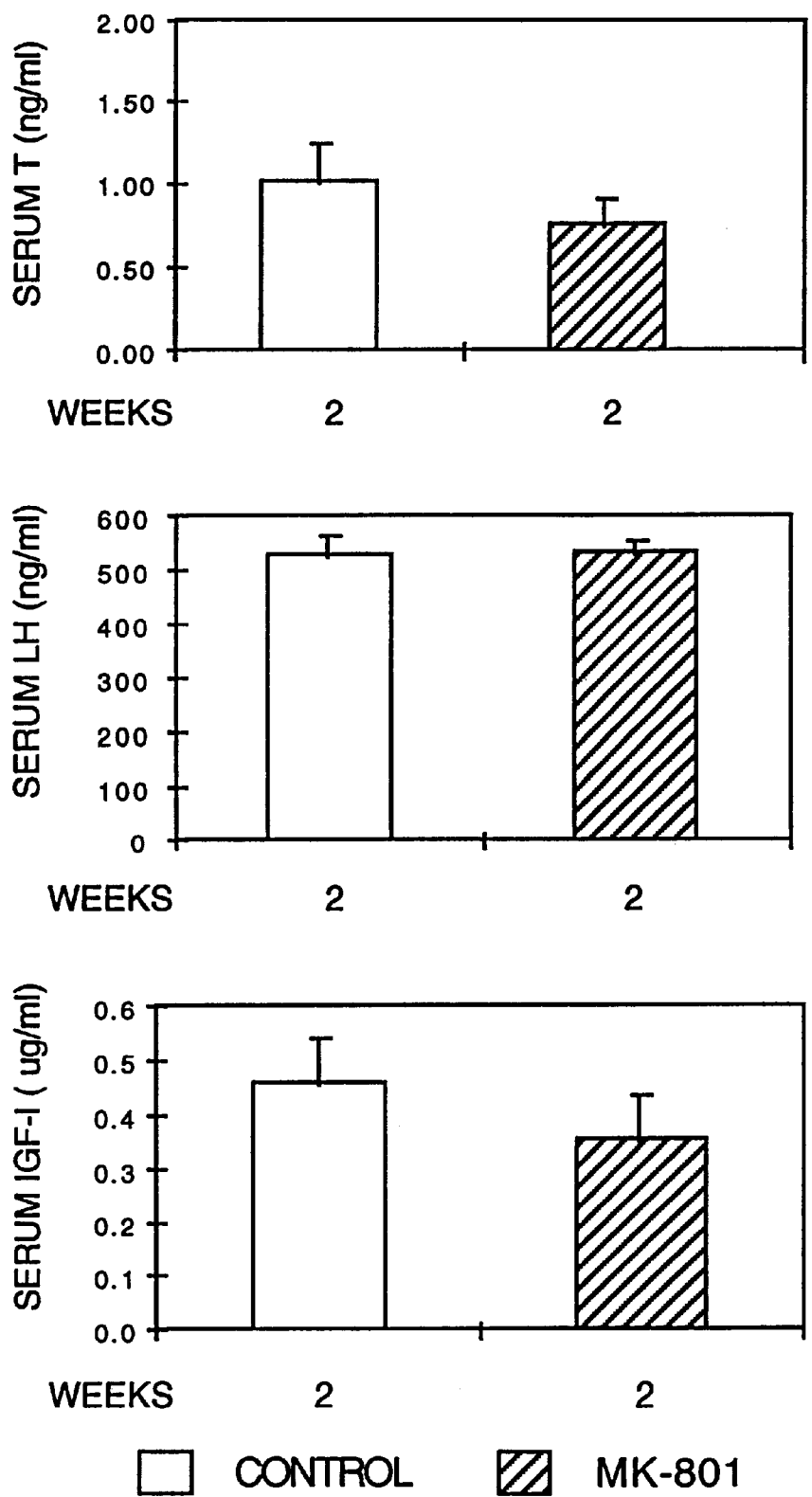
FIG. 5 shows the effect of NMDAR blockade by MK-801 in adult rats on serum T, LH, and IGF-1.

FIG. 5 (next page) shows that, as in the case of the immature animals, NMDAR blockade for 2 weeks in adult rats does not significantly affect either serum T, or LH. In contrast to the immature rats, no change was seen in serum IGF-1 levels. These results indicate that the inhibition of prostate growth is not due to interference with the gonadal/hypothalamic/pituitary axis.

EXAMPLE 2

This example demonstrates that NMDARs are present in both the rat and human prostate and bladder. Adult male rats (N=3) were anesthetized and sacrificed to remove the bladder and ventral prostate. 20–40 mg tissue from the organs from one rat were homogenized in a buffer (100–200 μl) containing 1% SDS-1 mM sodium vanadate-10 mM tris HCl pH 7.4, microwaving for 10–15 sec, and clarifying for 5 min at 12,500 g. This fraction was named total homogenate (THE). The remainder tissue, and the one obtained from the organs of the other two rats were homogenized at 4 C in a buffer containing protease inhibitors, and the post-mitochondrial (PM) and pellet fractions were separated by centrifugation at 15,000 g for 60 min, following a conventional procedure. The pellets were sequentially extracted with a buffer containing a mild detergent (20 mM Lubrol) followed by and a strong detergent (2% SDS). The extracts were named E1 and E2, respectively. The same procedures were applied to "normal" portions of human prostatic tissue obtained from open prostatectomies for prostate cancer, and to bladder tissue from cystectomies, that were transported in DMEM medium and frozen at arrival (within 2–3 hs after surgery) in liquid nitrogen.

Aliquots (40 μg protein) from each fraction were clarified by centrifugation at 12,000 g for 5 min, separated on denaturing 7.5% polyacrylamide gels, and subsequently transferred to nitrocellulose membrane by conventional electroblotting. The immunodetection was performed with a mouse monoclonal antibody against the 18 kDa protein fragment corresponding to amino acids 892–1051 of subunit 2B of the rat brain NMDAR (NMDAR2B). The secondary antibody was an antimouse IgG antibody linked to horse radish peroxidase, and visualization was performed with a luminol-based reaction followed by autoradiography.

Figure 6:
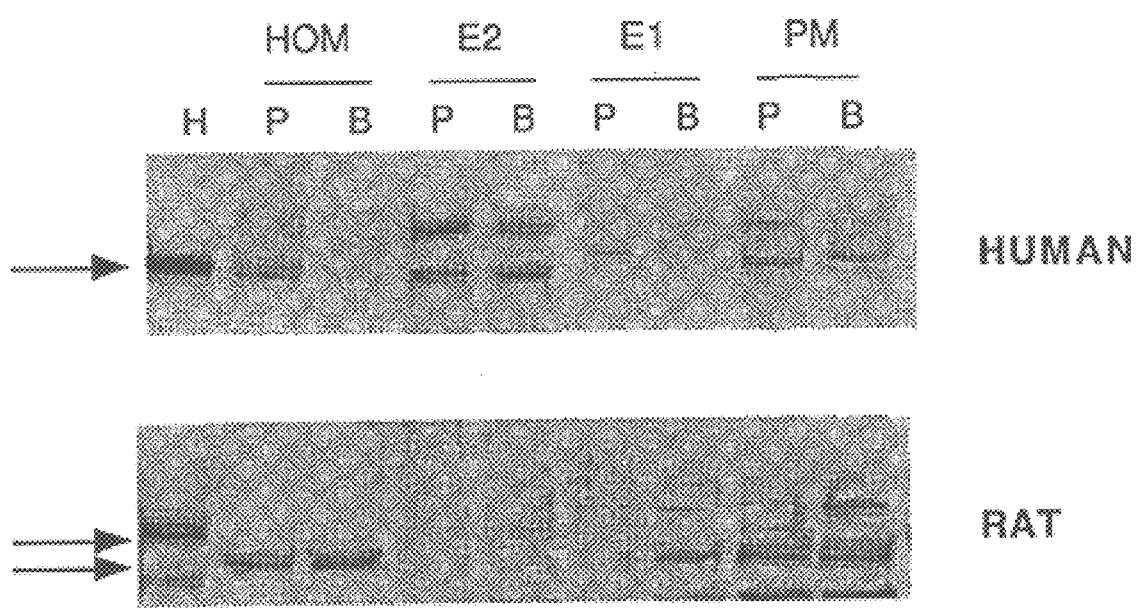
FIG. 6 shows the presence of NMDARs in the rat and human prostate and bladder detected by western blot assay.

FIG. 6 presents the X-rays for two separate gels. In the first one (top panel), the expected 180 kDa band for the rat NMDAR2B is seen in the extract from the rat hypothalamus (H), accompanied by a smaller band (approx. 130 kDa) that is likely to correspond to one of the 5' splicing products previously described. In the case of the human prostate (P), a strong signal of the expected size is present in the SDS extracts of membrane pellets (E2), accompanied by a larger band absent in H. The putative NMDAR protein is scarcely seen in the post-mitochondrial (PM) and lubrol extracts of membrane pellets (E1), but it can be detected in unfractionated homogenates (HOM). In the rat prostate, the band is smaller than in the human counterpart (140 kDa), possibly due to other alternate variants seen in brain. In addition, the subcellular location is different, because it is present in PM instead of E2. The rat and human bladder (B) has an NMDAR2B protein subcellular distribution and concentration similar to the prostate.

This western blot, and the ones not shown reproducing this result, indicates that NMDAR is expressed in the human prostate and bladder, thus explaining the relaxation effects exerted by NMDAR blockers on prostate and bladder strips in organ bath (see below). Most likely this expression occurs in the rat prostate and bladder as well, in the form of a shorter 2B subunit that may be a product of tissue-specific splicing. Similar proteins appear to be present in the rat (reduced length) and human (normal length) penis, agreeing with the observed response of the three types of tissue in organ bath to NMDAR blockers (see below).

In another experiment, tissue membranes were obtained from the rat and human prostate and bladder, by taking approximately 1 g of tissue (pools in the case of rat organs) and applying a conventional procedure to isolate a "crude" membrane fraction. This method is designed for synaptosomal membrane preparations from brain tissue. In this experiment, as well as in the organ bath studies, rats were sacrificed by decapitation to avoid using the conventional anesthetic (ketamine) that is a NMDAR antagonist and may compete in the binding experiments. Aliquots equivalent to 8 mg tissue were incubated for 60 min at 4C in a medium containing a saturating concentration (2 nM) of the NMDAR ligand (3H)-CGP and the bound ligand was separated from the excess free ligand by vacuum filtration on glass fiber filter discs. The discs were counted for radioactivity in a liquid scintillation counter. Similar incubations were carried out in the presence of a large excess of nonradioactive L-glutamate (100 μM), and the unspecific radioactivity was subtracted. Each determination was performed in triplicate.

Figure 7:
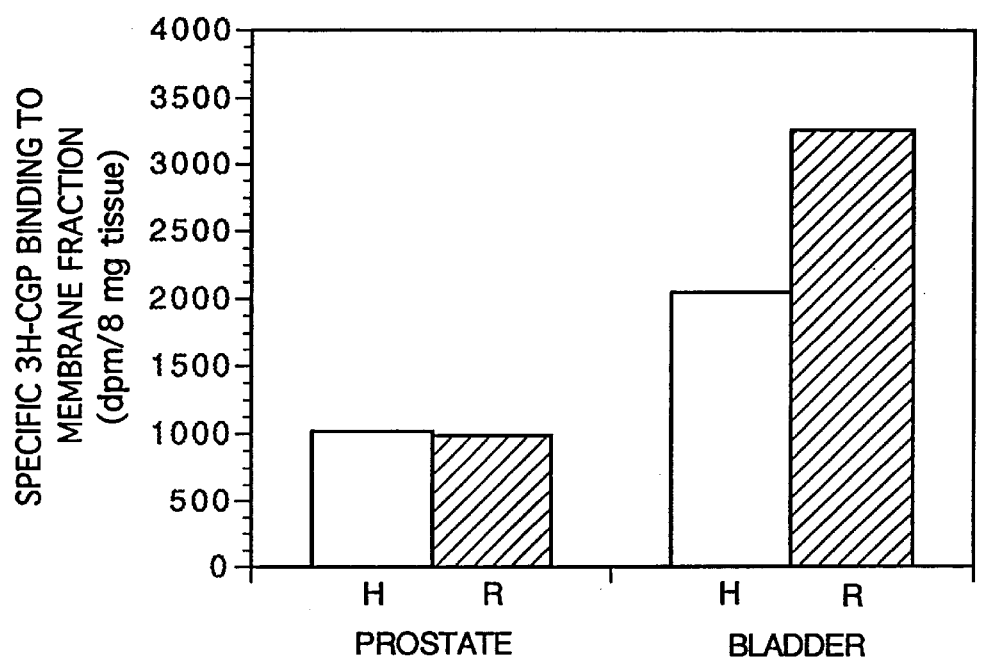
FIG. 7 shows the presence of NMDARs in the rat and human prostate and bladder detected by a ligand binding assay.

FIG. 7 shows that both the human (H) and rat (R) prostate membranes bind (3H)-CGP to the same extent, and that the same occurs with the membrane preparations from the human and rat bladder. However, the bladder is more active than the prostate, in agreement with the much better response of bladder tissue to relaxation by NMDAR antagonists in organ bath (see below). This experiment indicates that the NMDAR protein detected by western blot is active in binding a specific ligand of the NMDAR and that this reaction is competed by an excitatory amino acid (L-glutamate), demonstrating the existence of functional NMDAR or NMDAR-like proteins in the prostate and bladder.

EXAMPLE 3

This example demonstrates that the blockade of the NMDAR by an antagonist can relax reversibly in vitro preparations of rat and human bladder tissue submitted to pre-contraction, in a process that is not dependent on the release of nitric oxide.

Strips from the bladder body (detrusor) from adult (5 month-old) male rats were used for organ bath studies where the isometric tension generated during contraction/relaxation cycles was measured under different pharmacological and EFS treatments in 10 ml Krebs/Ringer/bicarbonate under standard conditions. The pattern of responses are shown below on continuous recordings obtained on a computer equipped with a data acquisition system, with the exception of periods of washing (W) and equilibration (15–20 min). The Y axis corresponds to an arbitrary scale where 0.455 is equivalent to I g. If not stated otherwise KCL (K) and bethanechol (B) are used at 140 and 0.3 mM final concentrations, respectively. The optimum concentration of bethanechol was obtained in dose response curves done as preliminary experiments (not shown).

Figure 8:
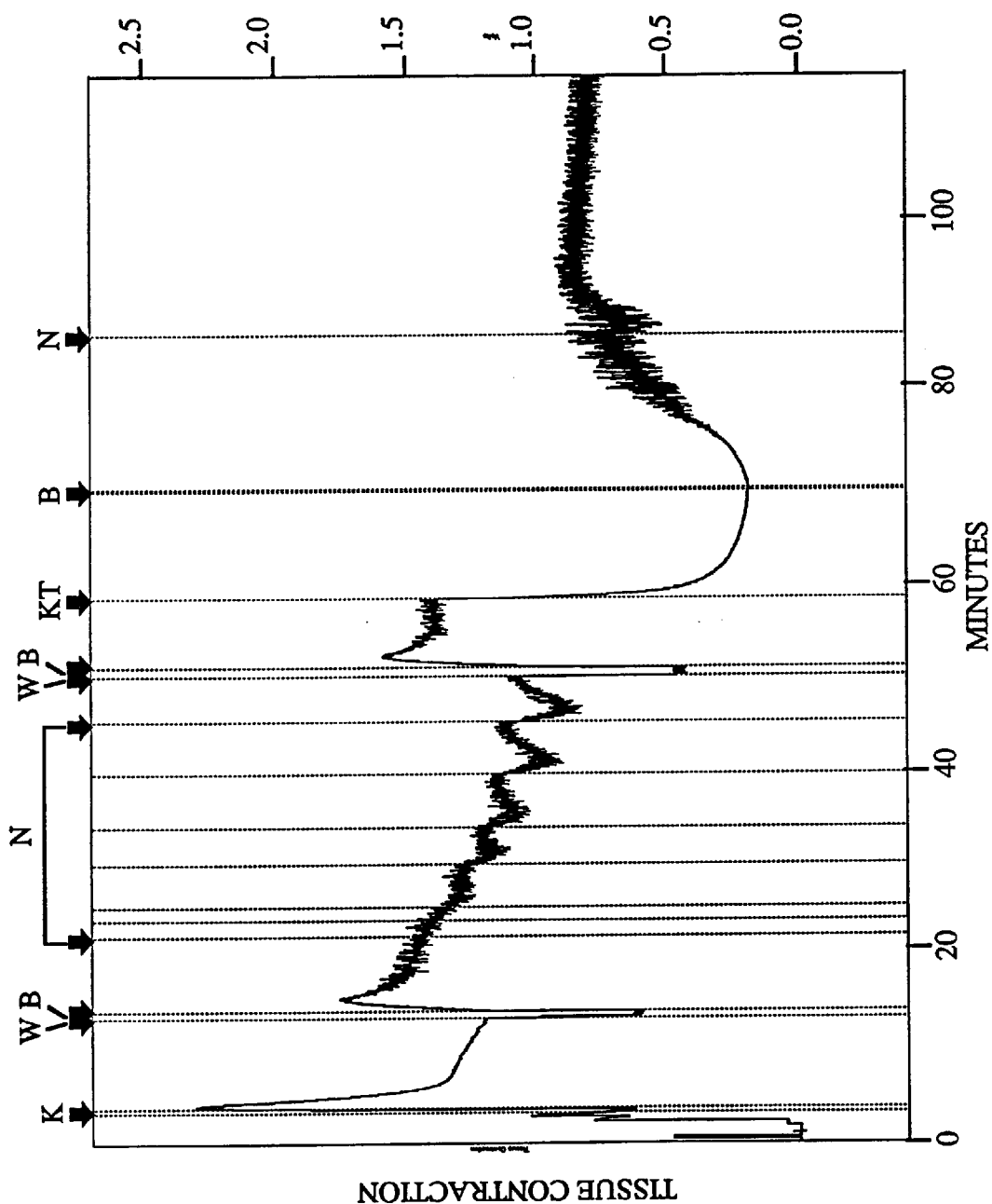
FIG. 8 shows the effect of NMDA and an NMDAR antagonist (ketamine) on the tone of rat bladder strips in vitro.

FIG. 8 shows a good contractile response with KCl, followed after washing by a lower response to bethanechol. These responses are in general of short duration and the tissue relax slowly after the peak of contraction. The addition of increasing concentrations (0.05–10 mM) of the excitatory amino acid NMDA (N) to the bethanechol-contracted strips undergoing the relaxation stage induced a series of small contractions of increasing intensity, followed by a continuation of the relaxation ("V" signals). After washing and contracting again with bethanechol, the spontaneous relaxation was minimal and a plateau was achieved. When the NMDA receptor antagonist, ketamine (KT) was added at 1 mM, a dramatic relaxation occurred that attenuated further contraction with bethanechol, although NMDA induced the "V" response previously seen.

Figure 9:
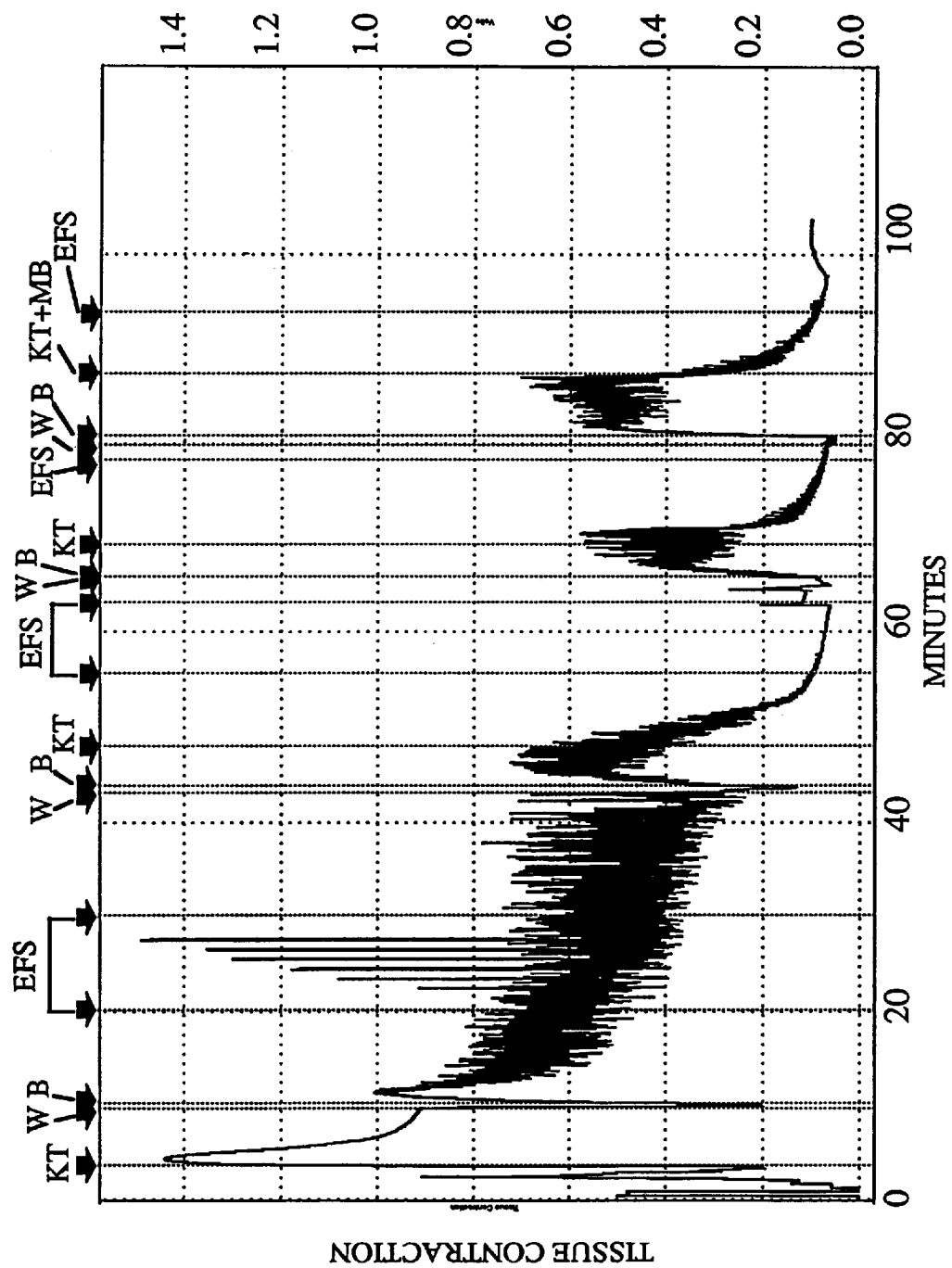
FIG. 9 shows that the effect of ketamine on the tone of rat bladder strips in vitro is not mediated by the nitric oxide cascade.

FIG. 9 shows the response obtained with bladder tissue from a second rat. After the KCl and bethanechol responses, EFS was applied at frequencies ranging from 2 to 64 Hz, and the expected high contractility was observed. Following washing, the tissue was contracted with bethanechol and again a complete relaxation was achieved. The relaxed tissue was completely insensitive to EFS. This cycle was repeated, and finally the bethanechol-contracted tissue was shown to relax with ketamine, even in the presence of 30 $\mu$M methylene blue (MB), an inhibitor of guanyl cyclase, thus discarding an NO-dependent pathway. Dose curves with ketamine (0.02–2 mM) were done in another rat (not shown), confirming the relaxation ability.

Figure 10:
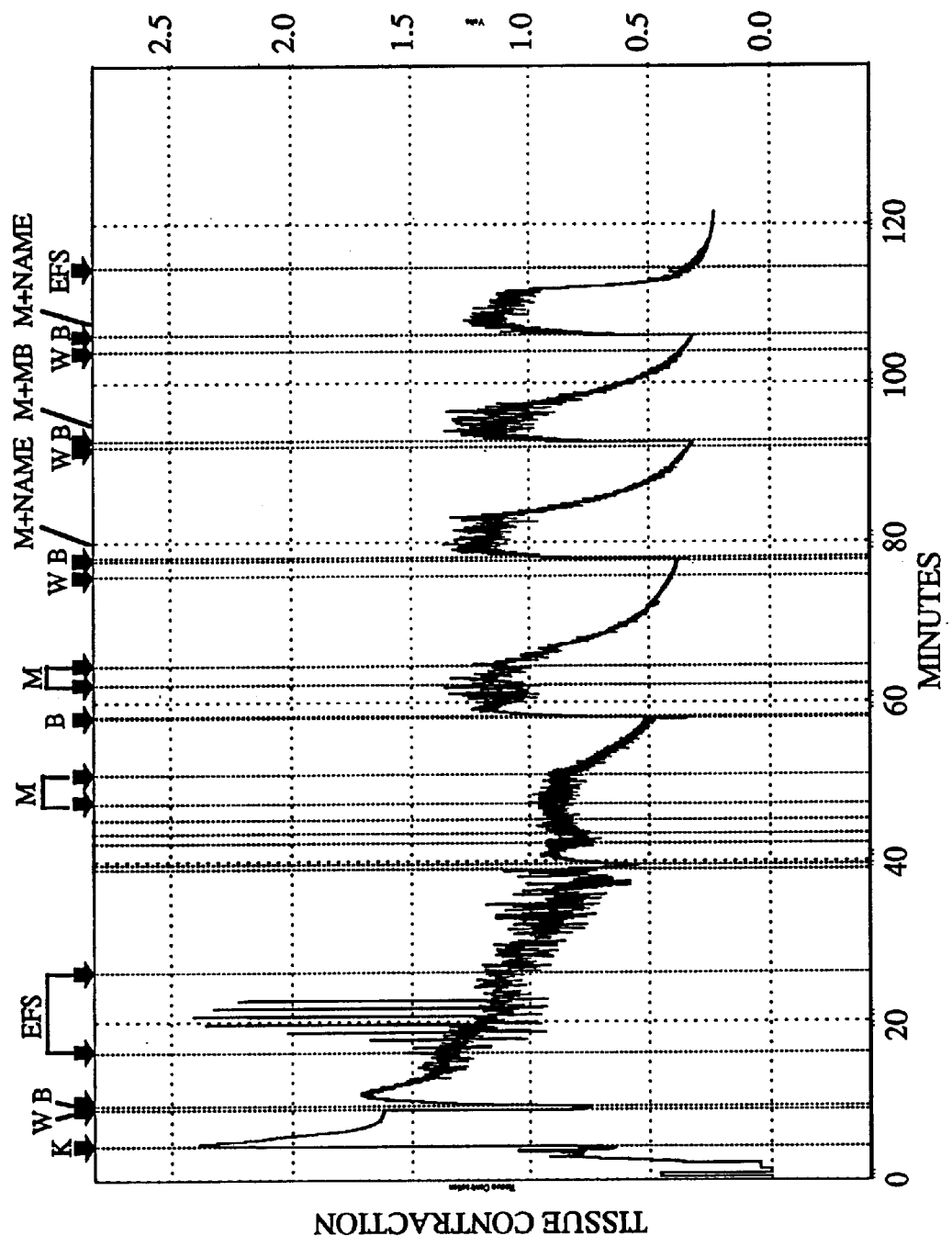
FIG. 10 shows the effect of another NMDAR antagonist (MK-801) on the tone of rat bladder strips in vitro and confirms the independence from the nitric oxide cascade.

FIG. 10 shows the response obtained with bladder tissue from a third rat. Essentially the same response as before was obtained with KCl, bethanechol, EFS, washing, bethanechol, and then a relaxation with increasing doses from 0.003 to 0.7 mM of another NMDA receptor antagonist, MK-801 (M). This relaxation counteracts the EFS response, is reversible with bethanechol, resistant to the nitric oxide synthase (NOS) inhibitor L-NAME and to methylene blue, and can be repeated several times after washing and bethanechol contraction.

A series of 8 more rats have been studied, showing essentially the same pattern of response that demonstrates the ability of the pre-contracted rat bladder to completely relax to at least two NMDAR antagonists, and when it is under spontaneous relaxation to undergo short contractile episodes with the NMDAR agonist. The ability of an additional series of NMDAR antagonists to relax pre-contracted strips of bladder detrusor from both male and female rats was also demonstrated specifically for antagonists of the NMDAR transmitter site, such as D-AP-7 and pentamidine, of the polyamine site, such as ifenprodil, and of the ion channel (low affinity), such as memantidine, amantidine, and dextromethorphan.

In order to determine whether the blockade of the NMDAR may induce the relaxation of human bladder tissue, the experiments described above were repeated with isolated detrusor strips from human bladder. This tissue was obtained after informed consent.

Figure 11:
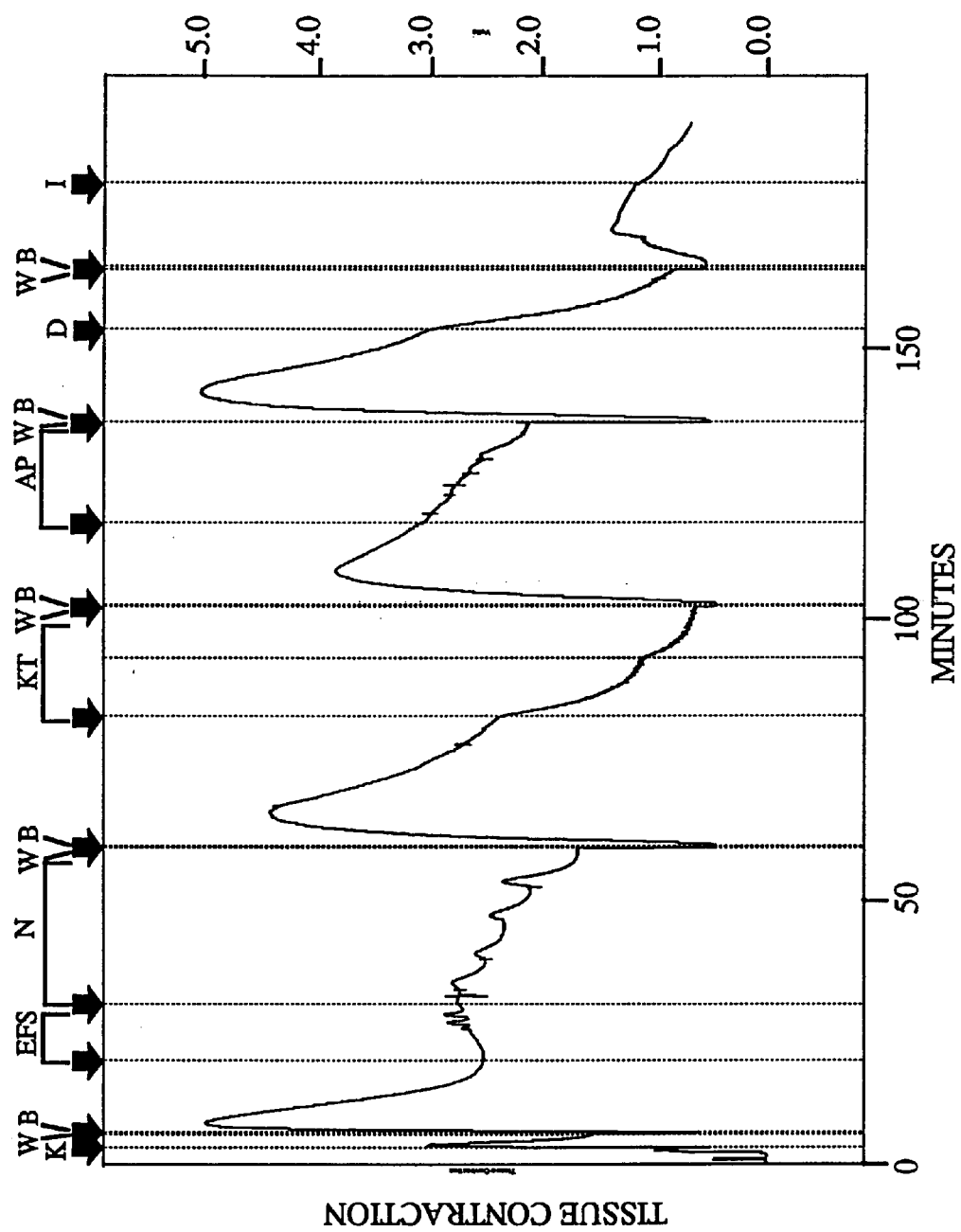
FIG. 11 shows the effect of ketamine and other NMDAR antagonists (AP-5, dextromethorphan, ifenprodil) on the tone of human bladder strips in vitro.

FIG. 11 shows the excellent contraction achieved with bethanechol, and paradoxically the poor response to EFS (as compared to the rat bladder). Increasing concentrations of NMDA as above led to similar short contractile responses as in the case of the rat bladder. After washing and bethanechol contraction/spontaneous relaxation, the tissue was totally relaxed with increasing concentrations of ketamine. The same, or even more intense effects, were obtained with other NMDA receptor blockers, such as 0.01–1 mM 2-amino-5-phosphovalerate (AP5), 0.04–0.2 mM dextromethorphan (D), and 0.01–0.5 mM ifenprodil (I).

Strips from the bladder presented on FIG. 4 were maintained in medium at 4 C for 24 h, and the organ baths studies were then performed, following the same procedure as on FIG. 11.

Figure 12:
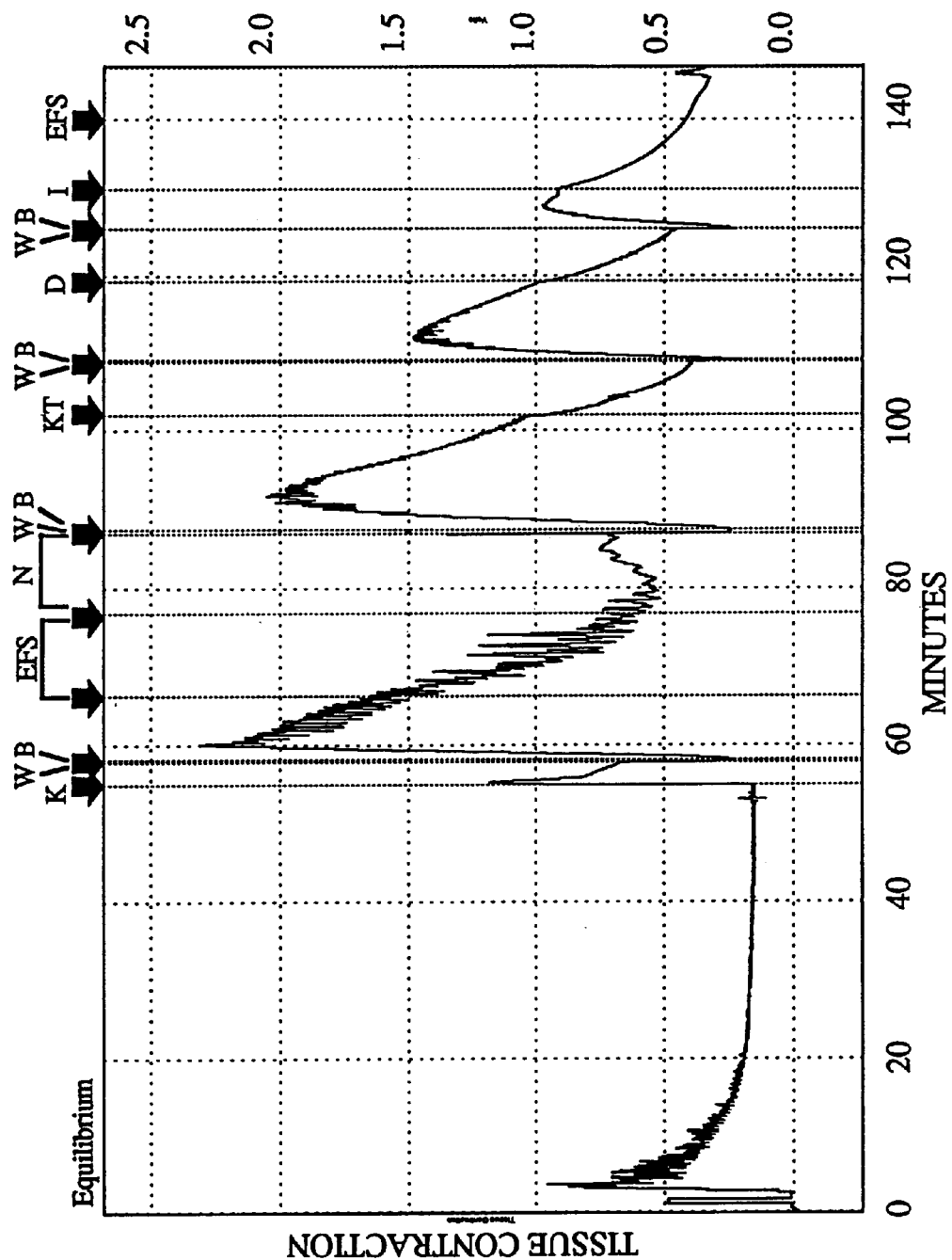
FIG. 12 shows the same effects as on FIG. 11 on the tone of "aged" human bladder strips in vitro (24 hs after excision).

FIG. 12 shows that essentially the same results were obtained with NMDA, ketamine, dextromethorphan, and ifenprodil, except that tissue fatigue was evident by a decrease with time of the contractile response to betanechol.

These experiments demonstrate that human bladder reacts essentially as the rat organ to the NMDA agonists (contraction) and antagonists (relaxation), and suggest that the latter drugs may be useful for the treatment of bladder instability and hypereflexia.

EXAMPLE 4

This example demonstrates that the blockade of the NMDAR by an antagonist can relax reversibly in vitro preparations of human prostate submitted to pre-contraction, in a process that is not dependent on the release of nitric oxide.

Since the rat prostate is too fragile, this tissue could not be used for performing experiments in organ bath and only human tissue could be used. Strips of human prostate transitional zone obtained by open prostatectomy after informed consent and were submitted to the same treatments as above, except that pre-contraction was exerted with norepinephrine instead of betanechol.

Figure 13:
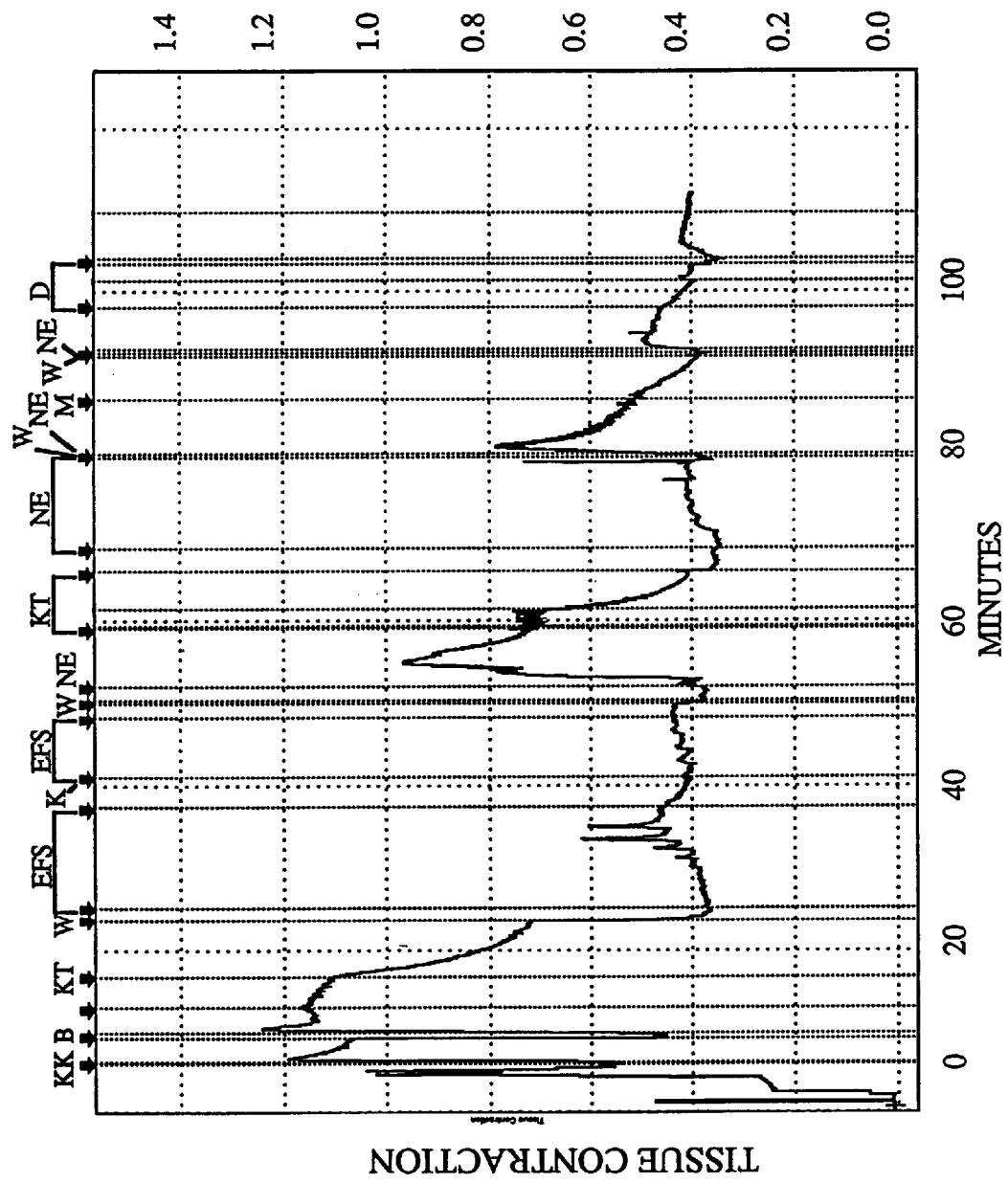
FIG. 13 shows the effects of ketamine and dextromethorphan on the tone of isolated strips of human prostate obtained by open prostatectomy.

FIG. 13 shows that the transitional zone prostatic tissue contracts well with KCl and with 0.2 mM norepinephrine (NE) and then relaxes completely with 1mM ketamine. After washing, the relaxed tissue responded little to EFS, but again contracted well with norepinephrine, relaxed to 1 mM ketamine, and while in its presence would not respond to a new addition of norepinephrine. However, after washing, the tissue regained its ability to contract with norepinephrine, and then it was relaxed by 0.25 mM MK801. An attempt to repeat the experiment with prostatic tissue maintained at 4 C for 24 h did not succeed, since the strips virtually did not respond to KCl or noradrenaline.

Another series of treatments were conducted with prostatic tissue obtained by TURP (transurethral resection of the prostate), trying to select only the non-charred sections in order to avoid artifacts.

Figure 14:
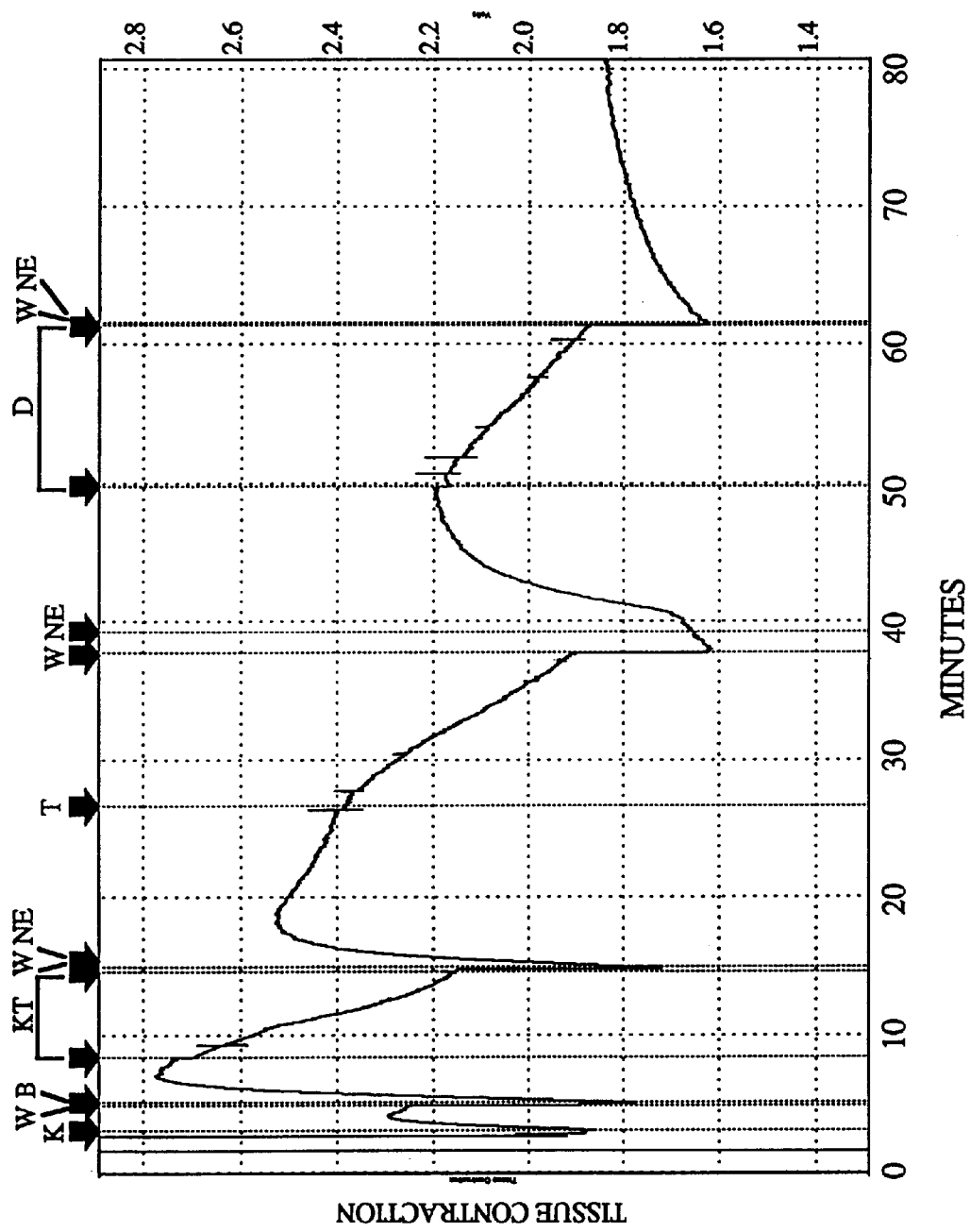
FIG. 14 shows the comparative effects of ketamine and dextromethorphan versus an alpha-adrenergic blocker (terazocine) on the tone of isolated strips of human prostate obtained by TURP.

FIG. 14 shows that the first contraction with KCl was moderate, but the one with norepinephrine was excellent. However, only a series of three contractile cycles of decreasing intensity could be studied, indicating tissue fatigue. Ketamine (1 mM) appeared to be more relaxing than 0.04 mM terazocin, and 0.2 mM dextromethorphan showed moderate effect. The terazocin was obtained by extraction of the 5 mg Hytrin tablets with Krebs, and clarification by centrifugation.

In order to get a better assessment of the effects induced by relaxant agents, an alternative assay was employed, where the prostatic tissue is first relaxed by addition of the compound to be tested and then the dose-response contraction by nor-epinephrine is determined and compared to that obtained in the absence of the relaxant agent. This procedure circumvents the problem created by spontaneous relaxation after norepinephrine, that not always leads to the gentle slope or plateau required to discriminate the steeper relaxation caused by the tested agent.

Figure 15:
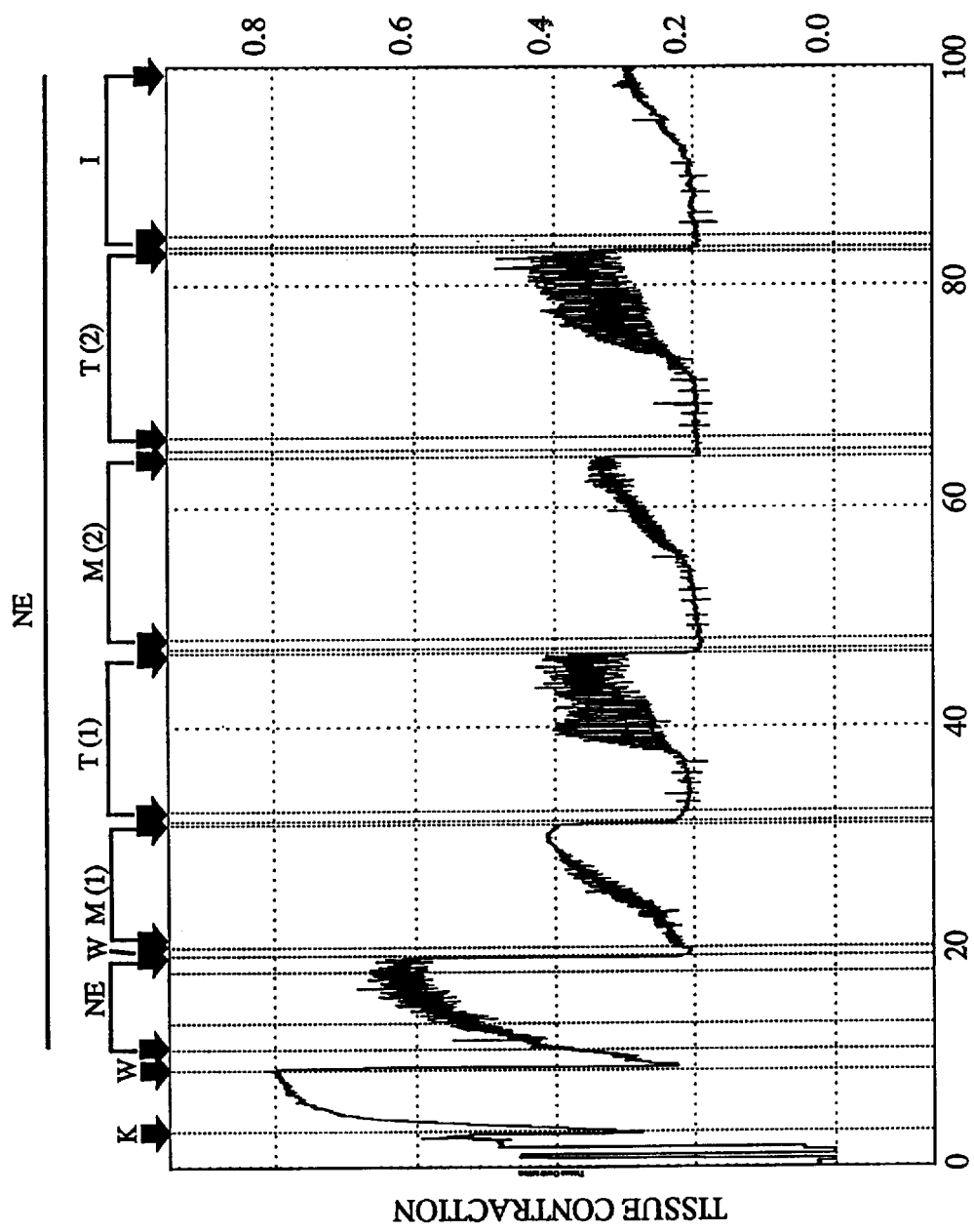
FIG. 15 shows the effects of MK-801 versus terazocine on the contractile response of human prostatic tissue to increasing concentrations of norepinephrine.

FIG. 15 shows first the contractile response to KCl of a strip of human prostatic tissue obtained by open prostatectomy, followed after washing by a measurement of the successive contractions caused by increasing cumulative concentrations of norepinephrine (1 to 50 $\mu$M). The dose response curve to norepinephrine was then repeated (1 to 100 $\mu$M) in the presence of the following substances, separating each treatment by a washing and equilibration period: 300 $\mu$M MK-801 (M-1); 20 $\mu$M terazocin (T-1); 75 $\mu$M MK-801 (M-2); 7 $\mu$M terazocin (T-2); 35 $\mu$M ifenprodil (I). It is noteworthy that the contractions elicited by norepinephrine in the presence of terazosin led to a continuous succession of relaxation/contraction cycles causing a considerable noise in the recording. MK-801, and particularly ifenprodil, showed as active in counteracting the contractions as compared to terazocin, although in molar terms their potency may be lower than that of the control drug. However, complete dose-response curves need to be done to determine the actual relative in vitro potency, and compare it with the therapeutic index in vivo.

These experiments show that the NMDAR blockers are efficient prostate relaxing agents and lead to the proposal that they may be have therapeutic value for BPH either per se or in conjunction with anti-alpha-adrenergic receptor compounds.

EXAMPLE 5

This example demonstrates that the blockade of the NMDAR by an antagonist can relax reversibly in vitro preparations of human penile corpora cavemosa submitted to pre-contraction, in a process that is not dependent on the release of nitric oxide.

Pieces from human corpora cavemosa were excised after informed consent from impotent patients undergoing penile prosthesis implantation. The tissues were transported to the laboratory as above, cut in 0.5×0.3×0.3 cm strips, washed in Krebs/Ringer bicarbonate buffer, and used within 2–4 h of excision (unless stated otherwise) for organ bath studies. The isometric tension was measured as above. If not stated otherwise KCL (K) and phenylephrine (PE) were used at 140 and 0.01 mM final concentrations, respectively.

Figure 16:
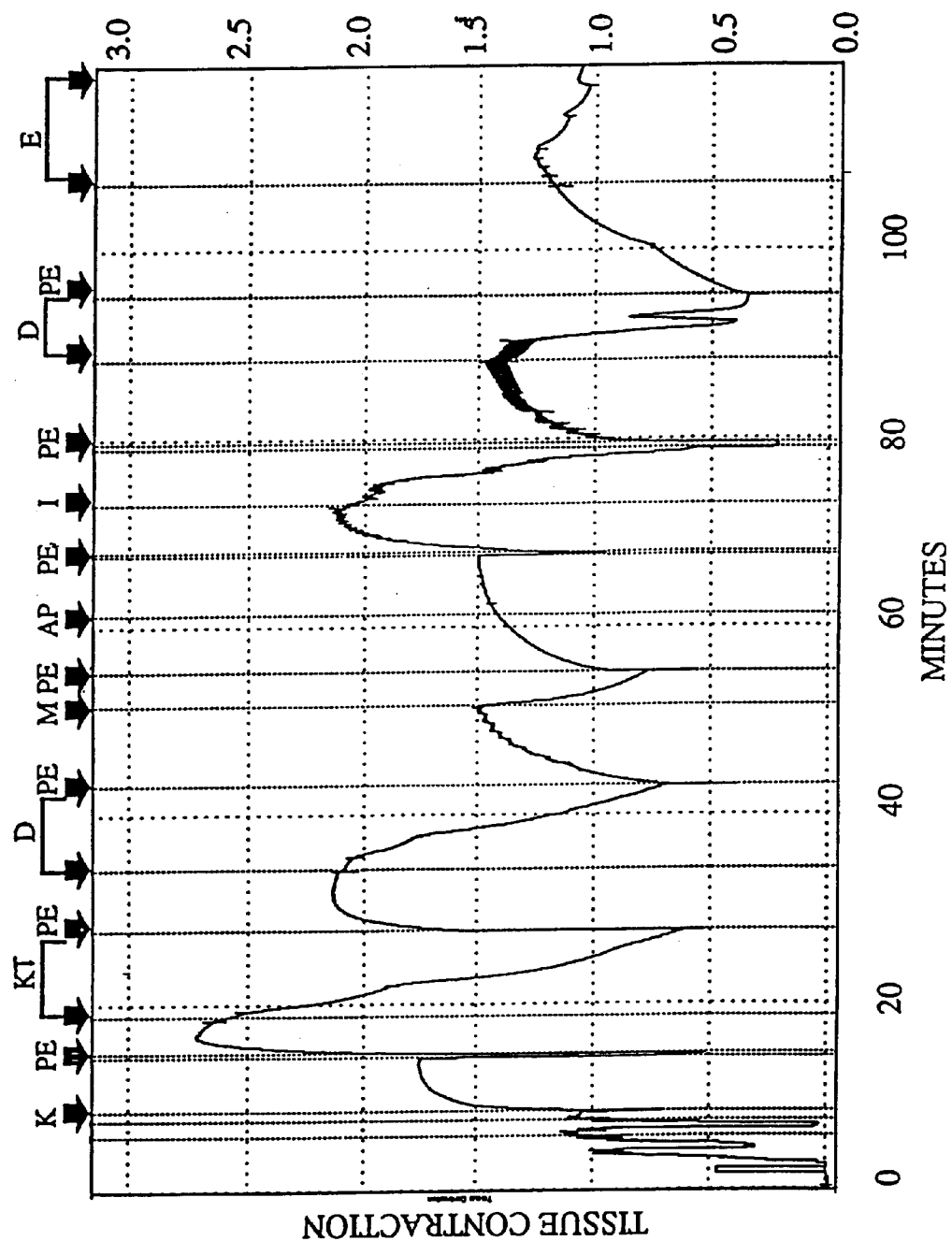
FIG. 16 shows the effects of ketamine, MK-801, and dextromethorphan on the tone of isolated strips of human corpora cavernosa.

FIG. 16 shows a good contractile response with KCl, followed after washing by a higher response to PE that is relatively stable. When the NMDA receptor antagonist, ketamine (KT) was added at increasing cumulative concentrations (0.07, 0.35, 1.1 mM), leading to a considerable relaxation at 0.35 mM and a complete one at 1.1 mM. A similar response was seen, after washing an new contraction with PE, by adding other NMDA blocker, dextromethorphan (D), at 8,40, 120, and 240 $\mu$M, with an already pronounced effect at 40 $\mu$M. Surprisingly, 2-amino-5-phosphovalerate (AP), acting at the NMDA transmitter site and tested up to 1 mM, did not inhibit the contraction exerted by PE. In contrast, ifenprodil (I), tested at 2.5, 12.5, and 38 $\mu$M, was a very potent inhibitor at even the minimum dose.

Figure 17:
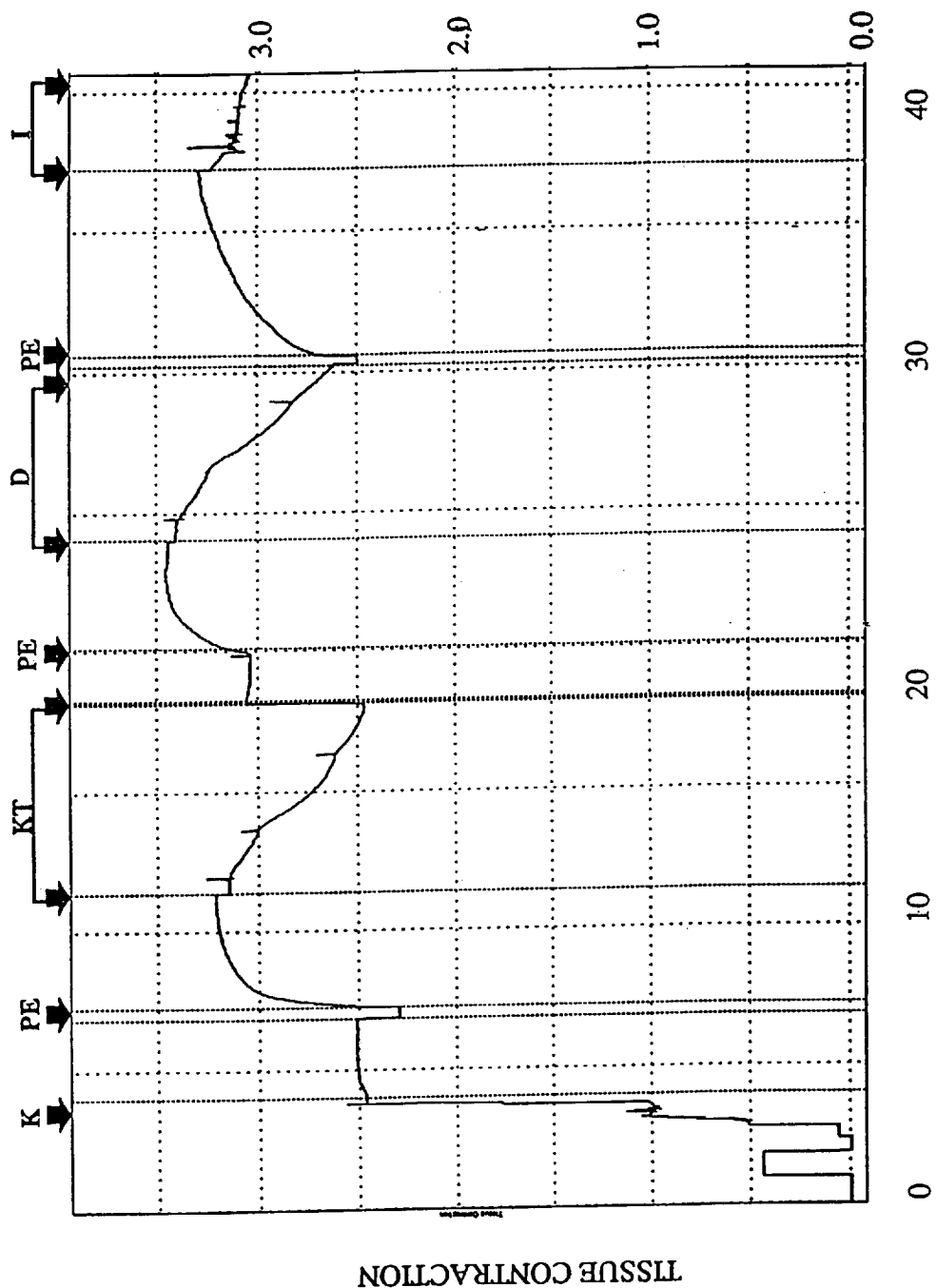
FIG. 17 shows the effects of ketamine and dextromethorphan on the tone of aged isolated strips of human corpora cavernosa (24 hours after excision).

FIG. 17 shows that the assay needs to be done the same day of penile tissue excision because after 24 h of storage in medium at 4 C, although the contractions with both K+ and PE are reasonable, the strips do not spontaneously relax to the base line after washing. However, even under these sub-optimal conditions the relaxations exerted by ketamine, dextromethorphan and ifenprodil, were as expected, reaching the base line obtained by spontaneous relaxation. Concentrations were as in the experiment depicted on FIG. 1.

Figure 18:
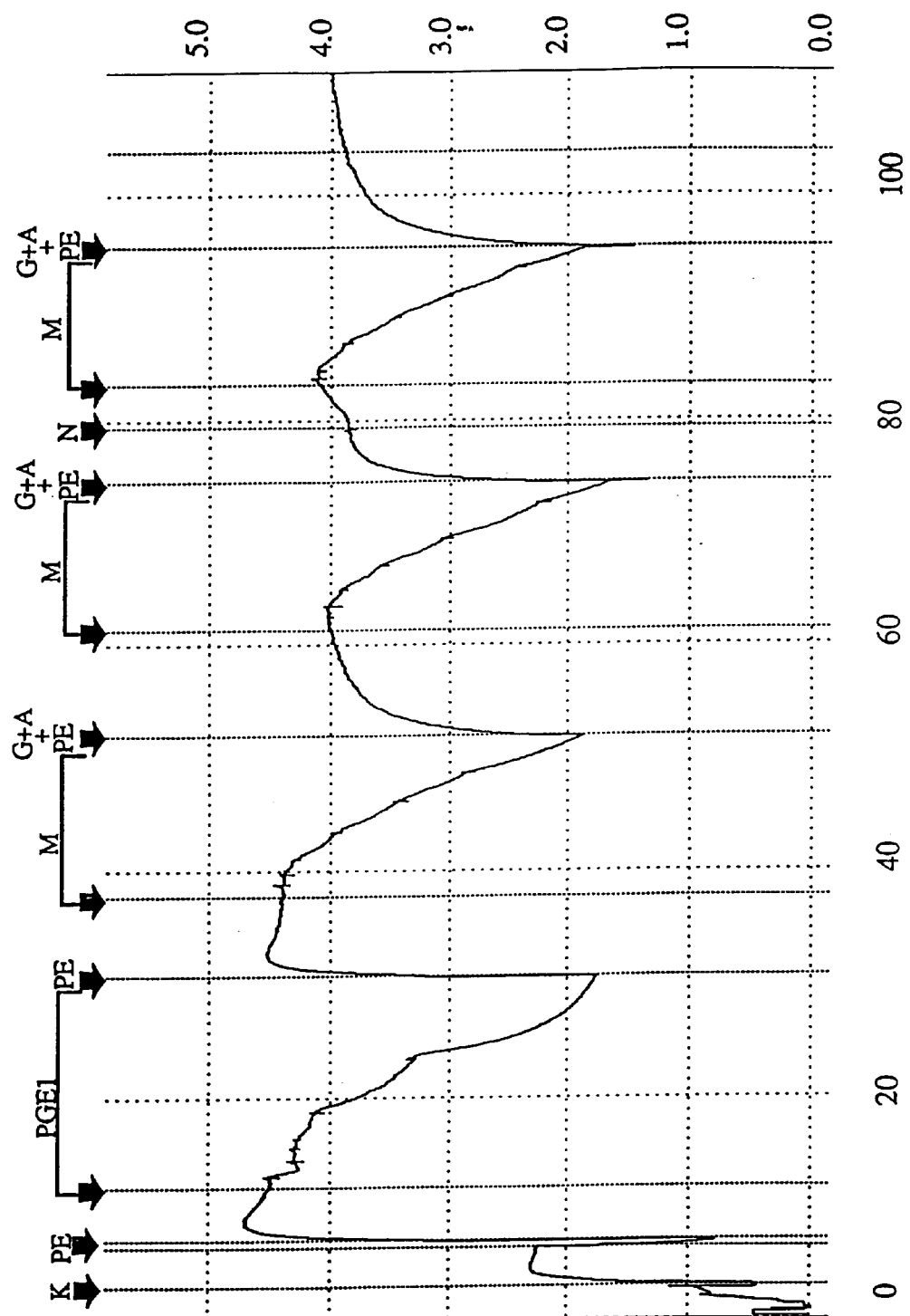
FIG. 18 shows the effects of MK-801 in comparison to a reference cavernosal relaxant, PGE-1, on the tone of isolated strips of human corpora cavernosa.

FIG. 18 corresponds to a second human corpora cavernosa specimen. After satisfactory K+ and PE contractile responses, the widely used relaxant PGE1 was added at increasing cumulative concentrations (0.3 to 56 $\mu$M, or 0.1 to 20 $\mu$g/ml), obtaining a total relaxation only at the maximal concentration. After washing and PE contraction the test was repeated by adding MK801 (M) at 3.5, 17.5, 53, 106, 180, and 360 $\mu$M, showing that a concentration of 53 $\mu$M the relaxation was equivalent to that elicited by 23 $\mu$M PGE1. This is a NANC response, as indicated by the fact that it is not inhibited by previous addition of 5$\mu$M guanethidine/40 $\mu$M atropine (G+A). The relaxation is neither mediated by the NO pathway as shown by simultaneous addition of the nitric oxide synthase inhibitor L-NAME (1 mM) together with G+A (N+G+A).

These experiments show that the NMDA blockers are efficient penile relaxing agents and suggest that they may be have therapeutic value for impotence either per se or in conjunction with other compounds currently in use for the therapy of erectile dysfunction.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A method for treating the abnormal growth of prostatic tissue in a person with benign prostatic hyperplasia, comprising locally administering to the prostatic tissue of the person at least one compound that is an antagonist of N-methyl-D-aspartate receptors selected from the group consisting of memantidine, amantidine, dextromethorphan and ketamine, wherein the mode of administration is by injection, continuous infusion, intraurethral delivery, prostate lavage, urethral lavage or topical.

2. The method of claim 1, wherein said step of administering said at least one compound that is an antagonist of N-methyl-D-aspartate receptors comprises administering a plurality of compounds that are antagonists of N-methyl-D-aspartate receptors in combination.

3. A method for treating the abnormal growth of prostatic tissue in a person with benign prostatic hyperplasia, comprising locally administering to the prostatic tissue in the person at least one compound that is an antagonist of N-methyl-D-aspartate receptors, said at least one compound being selected from the group consisting of memantidine, amantidine, dextromethorphan, and ketamine.

* * * * *

UNITED STATES PATENT AND TRADEMARK OFFICE
CERTIFICATE OF CORRECTION

PATENT NO. : 6,133,281
DATED : Oct. 17, 2000
INVENTOR(S) : Nester F. Gonzalez-Cadavid, Jacob Rajfer It is certified that error appears in the above-identified patent and that said Letters Patent is hereby corrected as shown below:

Title page, under Inventors:, second line, delete "A.", after "Jacob".

Title page 2, second column, eleven lines down after "for", insert --the Lower Urinary Tract, on Noradranaline Induced Contraction of Human Prostate and Meserteric Artery, J. Pharm. Exptl. Ther., 277: 1237-1247.--.

Column 7, line 28, after "channel.", sentence starting with "NMDAR" should be a new paragraph.

Signed and Sealed this

First Day of May, 2001

Attest:

NICHOLAS P. GODICI

Attesting Officer    Acting Director of the United States Patent and Trademark Office